United States Patent
O'Neill et al.

(10) Patent No.: US 10,934,267 B2
(45) Date of Patent: *Mar. 2, 2021

(54) ALPHA-TEA SALT FORMS: COMPOSITIONS AND USES FOR TREATING DISEASE

(71) Applicant: Research Development Foundation, Carson City, NV (US)

(72) Inventors: Michael O'Neill, Concord, OH (US); Barbara Kidon; Thomas Adkins, Concord, OH (US); Hongqiao Wu, Concord, OH (US); Emmanuel T. Akporiaye, Portland, OR (US)

(73) Assignee: Research Development Foundation, Carson City, NV (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/443,911

(22) Filed: Jun. 18, 2019

(65) Prior Publication Data

US 2020/0148661 A1    May 14, 2020

Related U.S. Application Data

(63) Continuation of application No. 14/916,271, filed as application No. PCT/US2014/054354 on Sep. 5, 2014, now Pat. No. 10,370,350.

(60) Provisional application No. 61/874,823, filed on Sep. 6, 2013.

(51) Int. Cl.
| | |
|---|---|
| *C07D 311/72* | (2006.01) |
| *A61K 31/355* | (2006.01) |
| *A61K 35/17* | (2015.01) |
| *A61K 39/395* | (2006.01) |
| *A61K 45/06* | (2006.01) |
| *C07C 215/08* | (2006.01) |
| *C07C 215/10* | (2006.01) |
| *C07C 229/26* | (2006.01) |
| *C07C 279/14* | (2006.01) |
| *C07K 16/32* | (2006.01) |

(52) U.S. Cl.
CPC .......... *C07D 311/72* (2013.01); *A61K 31/355* (2013.01); *A61K 35/17* (2013.01); *A61K 39/39558* (2013.01); *A61K 45/06* (2013.01); *C07C 215/08* (2013.01); *C07C 215/10* (2013.01); *C07C 229/26* (2013.01); *C07C 279/14* (2013.01); *C07K 16/32* (2013.01); *C07K 2317/24* (2013.01)

(58) Field of Classification Search
CPC ... C07D 311/72; C07C 229/26; C07C 279/14; C07C 215/10; C07C 215/08; C07K 16/32; C07K 2317/24; A61K 45/06; A61K 31/355; A61K 39/39558; A61K 35/17; A61P 35/00; A61P 31/00
See application file for complete search history.

(56) References Cited

U.S. PATENT DOCUMENTS

| | | |
|---|---|---|
| 6,417,223 B1 | 7/2002 | Sanders et al. |
| 6,703,384 B2 | 3/2004 | Sanders et al. |
| 6,770,672 B1 | 8/2004 | Sanders et al. |
| 7,300,954 B2 | 11/2007 | Sanders et al. |
| 7,312,232 B2 | 12/2007 | Sanders et al. |
| 7,608,638 B2 | 10/2009 | Sanders et al. |
| 7,718,814 B2 | 5/2010 | Sanders et al. |
| 8,148,424 B2 | 4/2012 | Sanders et al. |
| 8,664,264 B2 | 3/2014 | Sanders et al. |
| 10,370,350 B2 | 8/2019 | O'Neill et al. |

FOREIGN PATENT DOCUMENTS

| | | |
|---|---|---|
| JP | 46-29734 | 8/1971 |
| JP | 63-501569 | 6/1988 |
| JP | 2005-526705 | 9/2005 |
| WO | WO 1987/002219 | 4/1987 |
| WO | WO 2000/016772 | 3/2000 |
| WO | WO 2001/058889 | 8/2001 |
| WO | WO 2003/039461 | 5/2003 |
| WO | WO 2003-053407 | 7/2003 |

OTHER PUBLICATIONS

Anderson and Flora, In: The Practice of Medicinal Chemistry, ed. Wermuth, vol. 2, Chapter 34, pp. 347-365, 1999.
Anderson et al., "Differential response of human ovarian cancer cells to induction of apoptosis by vitamin E Succinate and vitamin E analogue, alpha-TEA," *Cancer Res*, 64(12):4263-4269, 2004.
Bastin et al., "Salt selection and optimization procedures for pharmaceutical new chemical entities," *Organic Process Research & Development*, 4:427-435, 2000.
Fariss et al., "The selective antiproliferative effects of alpha-tocopherl hemisuccinate and cholesterl hemisuccinate on murine leukemia cells result from the action of the intact compounds," *Cancer Research*, 54(13):3346-3351, 1994.
Guerrouahen et al., "GMP-grade α-TEA lysine salt: a 28-day oral toxicity and toxicokinetic study with a 28-day recovery period in beagle dogs," *BMC Cancer*, 16:199, 2016.
Hahn et al., "Dietary administration of the proapoptotic Vitamin E analogue alpha-tocopheryloxyacetic acid inhibits metastatic murine breast cancer," *Cancer Res*, 66:9374-9378, 2006.

(Continued)

*Primary Examiner* — Snigdha Maewall
(74) *Attorney, Agent, or Firm* — Parker Highlander PLLC

(57) ABSTRACT

The present disclosure relates to salts of the compound:

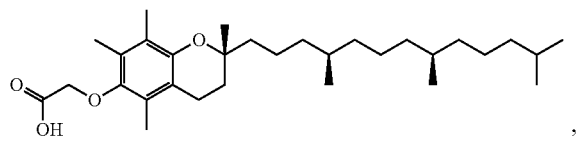

polymorphic forms thereof, methods for preparation and use thereof, and pharmaceutical compositions thereof.

16 Claims, 19 Drawing Sheets

(56) References Cited

OTHER PUBLICATIONS

Hahn et al., "Orally active alpha-tocopheryloxyacetic acid suppresses tumor growth and multiplicity of spontaneous murine breast cancer," *Mol Cancer Ther*, 8:1570-1578, 2009.

Kline, et al., "Vitamin E and cancer," *Vitam Horm*, 76:435-461, 2007.

Lawson, et al., "Novel Vitamin E analogue and 9-nitro-camptothecin administered as liposome aerosols decrease syngeneic mouse mammary tumor burden and inhibit metastasis," *Cancer Chemother Pharmacol*, 54:421-431, 2004.

Neuzil et al., "Vitamin E analogs, a novel group of "mitocans," as anticancer agents: the importance of being redox-silent," *Molecular Pharmacology*, 71(5):1185-1199, 2007.

Neuzil et al., "Vitamin E analogues as a novel group of mitocans: anti-cancer agents that act by targeting mitochondria," *Mol Aspects Med*, 28:607-645, 2007.

Neuzil et al., "Vitamin E analogues: a new class of inducers of apoptosis with selective anti-cancer effects," *Current Cancer Drug Targets*, 4(4):355-372, 2004.

Office Action issued in Japanese Application No. 2016-540431, dated Jan. 8, 2019, and English language translation thereof.

Office Action issued in Japanese Application No. 2016-540431, dated Apr. 25, 2018, and English language translation thereof.

PCT International Preliminary Report on Patentability issued in International Application No. PCT/US2014/054354, dated Mar. 17, 2016.

PCT International Search Report and Written Opinion issued in International Application No. PCT/US2014/054354, dated Dec. 17, 2014.

Shun et al., "Pro-apoptotic mechanisms of action of a novel vitamin E analog (α-tea) and a naturally occurring form of vitamin E (δ-tocotrienol) in MDA-MB-435 human breast cancer cells," *Nutrition and Cancer*, 48(1):95-105, 2004.

Trosko and Chang, "Mechanism of up-regulated gap junctional intercellular communication duling chemoprevention and chemotherapy of cancer", *Mutation Res*, 480-481:219-229, 2001.

Wang et al., "Vitamin E analogues as anticancer agents: lessons from studies with alpha-tocopheryl succinate," *Molecular Nutrition & Food Research*, 50(8):675-685, 2006.

Yu, et al., "α-TEA induces apoptosis of human breast cancer cells via activation of TRAIL/DR5 death receptor pathway," *Mol Carcinog*, 49:964-973, 2010.

ALPHA-TEA SALT FORMS: COMPOSITIONS AND USES FOR TREATING DISEASE

This application is a continuation of U.S. application Ser. No. 14/916,271, filed Mar. 3, 2016, which is a national phase application under 35 U.S.C. § 371 of International Application No. PCT/US2014/054354, filed Sep. 5, 2014, which claims the benefit of U.S. Provisional Application No. 61/874,823 filed on Sep. 6, 2013, the entirety of each of which is incorporated herein by reference.

BACKGROUND OF THE INVENTION

I. Field of the Invention

The present disclosure relates generally to salts of α-tocopheryloxyacetic acid (α-TEA), polymorphic forms thereof, and pharmaceutical compositions thereof. In other aspects, the present disclosure also relates methods for preparation and use of these substances.

II. Description of Related Art

Vitamin E analogs such as α-tocopheryloxyacetic acid (α-TEA) have been previously reported (U.S. Pat. Nos. 6,417,223, 6,703,384 B2, 6,770,672 B1, and 7,312,232 B2). The derivative α-TEA has been shown to suppress the growth of tumors through a mechanism which includes mitochondrial depolarization and the generation of reactive oxygen species which trigger cell death (Yu, et. al., 2010; Neuzil, et. al., 2007; Kline, et. al., 2007). Studies have shown that the compound inhibits the growth of a variety of different cancer cell lines without significant negative effects on normal tissues (Lawson, et al., 2003; Anderson, et al., 2004; Hahn, et al. 2009; Hahn, et al., 2006).

In view of these promising biological properties, and in consideration that biological activity profiles and physical properties can be expected vary across different salt forms of a compound, it remains desirable to obtain novel salts forms with advantageous properties, including one that may ease process scale-up and formulation issues and/or possess biological activity or pharmacokinetic profiles that is well suited for the treatment or prevention of a given disease or indication. In view of the high degree of unmet medical need represented by the diseases and indications discussed herein, it is therefore desirable to synthesize new solid forms, including salt forms, of α-TEA.

SUMMARY OF THE INVENTION

In one aspect, the present invention provides compounds of the formula:

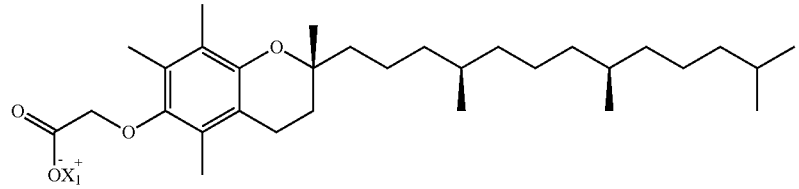

wherein $X_1^+$ is:

$Na^+$, $K^+$,

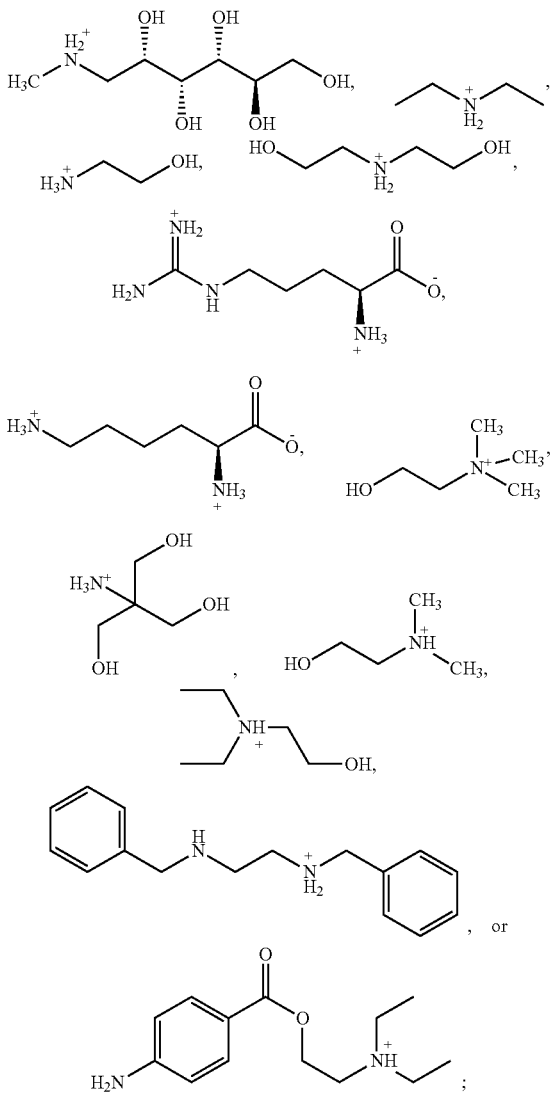

or a hydrate thereof. In some embodiments, $X_1^+$ is:

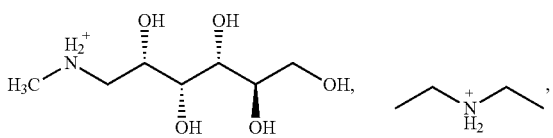

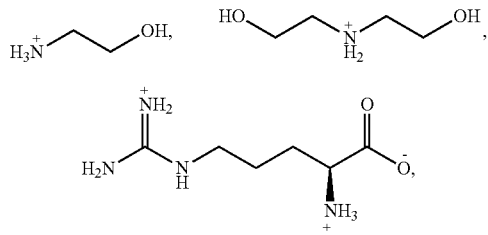
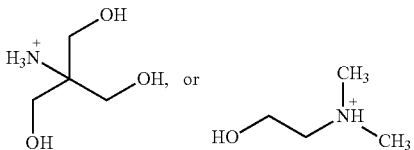

or a hydrate, thereof. In some embodiments, $X_1^+$ is

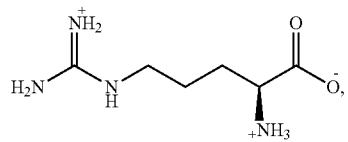

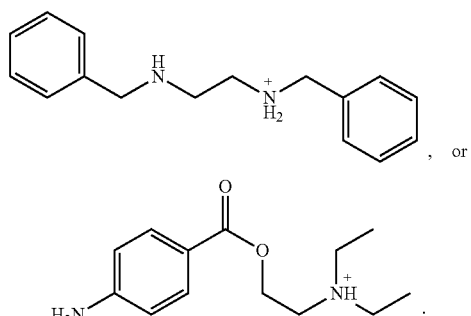
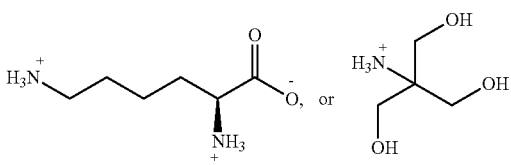

, or

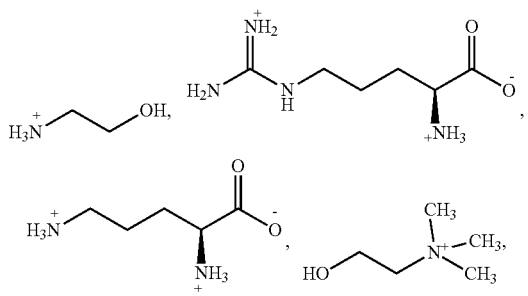

or a hydrate, thereof.

In some embodiments, the present disclosure provides a compound of the formula:

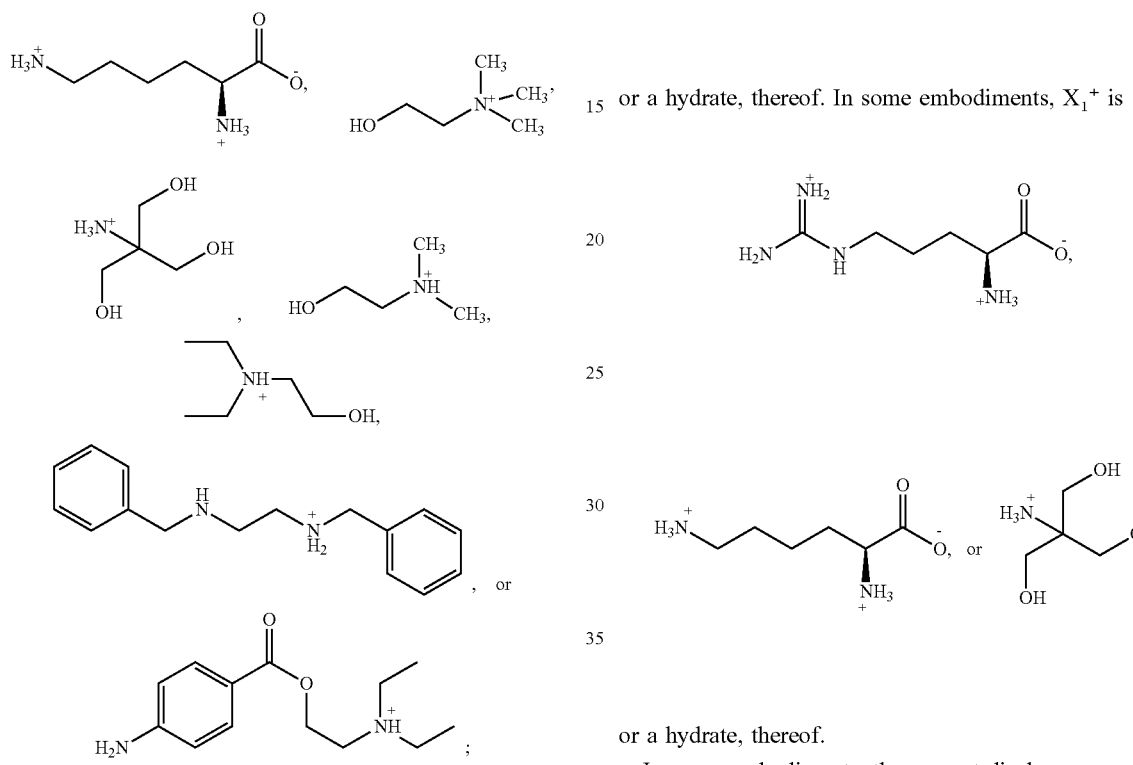

or a hydrate thereof. In some embodiments, $X_1^+$ is:

or a hydrate, thereof. In some embodiments, the compound is present as a polymorphic form having an X-ray powder diffraction pattern (CuKα) comprising two peaks at about 11.84°2θ and 19.74°2θ or a hydrate, thereof. In some embodiments, the polymorphic form has an X-ray powder diffraction pattern (CuKα) further comprising a peak at about 20.73°2θ. In some embodiments, the polymorphic form has an X-ray powder diffraction pattern (CuKα) further comprising 1, 2, 3, 4, 5, 6, 7, 8, 9, 10, 11, 12, 13, 14, 15, 16, or all of peaks at about 6.24, 9.35, 14.92, 15.51, 17.03, 18.49, 21.70, 22.81, 23.51, 24.85, 27.69, 28.31, 30.93, 32.30, 33.21, 35.02, and 39.30°2θ. In some embodiments, the polymorphic form has an X-ray powder diffraction pattern (CuKα) that is substantially as shown in FIG. 4. In some embodiments, the polymorphic form has a differential scanning calorimetry (DSC) isotherm comprising two endotherms from about 125° C. to about 140° C. and from about 170° C. to about 195° C. In some embodiments, the polymorphic form has a differential scanning calorimetry (DSC) isotherm comprising two endotherms centered at about 131° C. and at around 184° C., respectively. In some embodiments, the polymorphic form has a differential scanning calorimetry isotherm that is substantially as shown in FIG. 5. In some embodiments, the polymorphic form has a thermogravimetric analysis (TGA) indicating a total volatile content of about 0.3 wt % over the temperature range of about 25-194° C. In some embodiments, the polymorphic form has a dynamic vapor sorption (DVS) kinetic data and isotherm indicating a hemihydrate formation at about 40% relative humidity. In some embodiments, the polymorphic form is anhydrous. In other embodiments, the polymorphic form is a hydrate. In some embodiments, the polymorphic form is a hemihydrate.

In yet another embodiment, the present disclosure provides a compound of the formula:

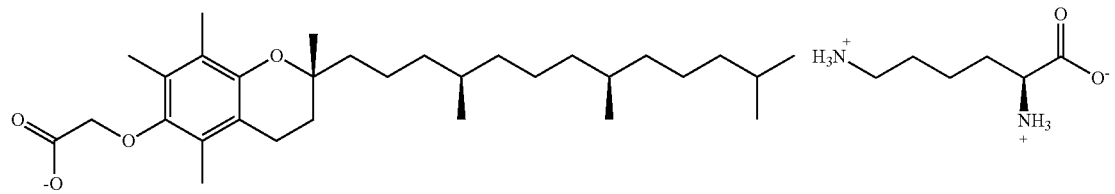

or a hydrate, thereof. In some embodiments, the compound is present as a polymorphic form having an X-ray powder diffraction pattern (CuKα) comprising a peak at about 9.69°2θ or a hydrate, thereof. In some embodiments, the X-ray powder diffraction pattern (CuKα) further comprises a peak at about 20.10°2θ. In some embodiments, the X-ray powder diffraction pattern (CuKα) further comprises a peak at about 19.78°2θ. In some embodiments, the X-ray powder diffraction pattern (CuKα) further comprises 1, 2, 3, 4, 5, 6, 7, 8, 9, 10, 11, 12, 13, 14, 15, 16, or all of peaks at about 5.90, 7.77, 14.08, 17.58, 17.91, 18.31, 21.26, 22.17, 23.16, 24.77, 28.57, 29.71, 31.10, 31.69, 34.45, 34.99, and 36.24°2θ. In some embodiments, the X-ray powder diffraction pattern (CuKα) that is substantially as shown in FIG. 6. In some embodiments, the polymorphic form has a differential scanning calorimetry (DSC) isotherm comprising two endotherms from about 53° C. to about 60° C. and from about 180° C. to about 235° C. In some embodiments, the polymorphic form has a differential scanning calorimetry (DSC) isotherm comprising two endotherms centered at about 55.8° C. and at about 205° C., respectively. In some embodiments, the polymorphic form has a differential scanning calorimetry isotherm that is substantially as shown in FIG. 7. In some embodiments, the polymorphic form has a thermogravimetric curve from thermogravimetric analysis (TGA) indicating a total volatile content of about 0.4 wt % over the temperature range of about 25-168.8° C. In some embodiments, the polymorphic form has a dynamic vapor sorption (DVS) kinetic data and isotherm indicating a hydrate formation above about 75% relative humidity. In some embodiments, the polymorphic form is anhydrous. In other embodiments, the polymorphic form is a hydrate.

In another embodiment, the present disclosure provides a compound of the formula:

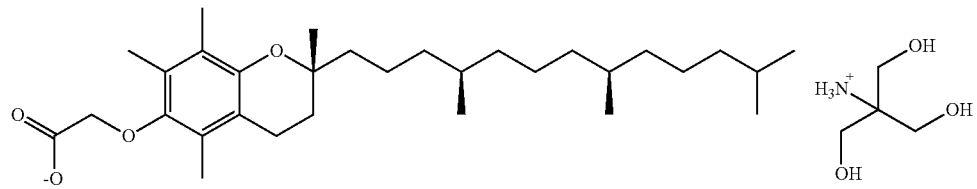

or a hydrate, thereof. In some embodiments, the compound is present as a polymorphic form having an X-ray powder diffraction pattern (CuKα) comprising a peak at about 20.14°2θ or a hydrate, thereof. In some embodiments, the X-ray powder diffraction pattern (CuKα) further comprises peaks at about 13.63, 14.40, 19.31, and 22.34°2θ. In some embodiments, the X-ray powder diffraction pattern (CuKα) further comprises two peaks at about 18.25 and 18.49°2θ. In some embodiments, the X-ray powder diffraction pattern (CuKα) further comprises 1, 2, 3, 4, 5, 6, 7, 8, 9, 10, 11, 12, or all of peaks at about 9.67, 15.60, 21.47, 23.57, 27.07, 28.39, 30.49, 32.21, 33.30, 34.29, 34.96, 35.89, and 36.39°2θ. In some embodiments, the polymorphic form has an X-ray powder diffraction pattern (CuKα) that is substantially as shown in FIG. 10. In some embodiments, the polymorphic form has a differential scanning calorimetry (DSC) isotherm comprising two endotherms from about 97.5° C. to about 120° C. and from about 185° C. to about 225° C. In some embodiments, the polymorphic form has a differential scanning calorimetry (DSC) isotherm comprising two endotherms at about 106° C. and at about 192° C., respectively. In some embodiments, the polymorphic form has a differential scanning calorimetry isotherm that is substantially as shown in FIG. 11. In some embodiments, the polymorphic form has a thermogravimetric curve from thermogravimetric analysis (TGA) indicating a total volatile content of about 0.6 wt % over the temperature range of about 25-144° C. In some embodiments, the polymorphic form has a dynamic vapor sorption (DVS) kinetic data and isotherm indicating a hemihydrate formation at about 55% relative humidity. In some embodiments, the polymorphic form is anhydrous. In other embodiments, the polymorphic form is a hydrate. In some embodiments, the polymorphic form is a hemihydrate.

In yet another embodiment, the present disclosure provides a compound of the formula:

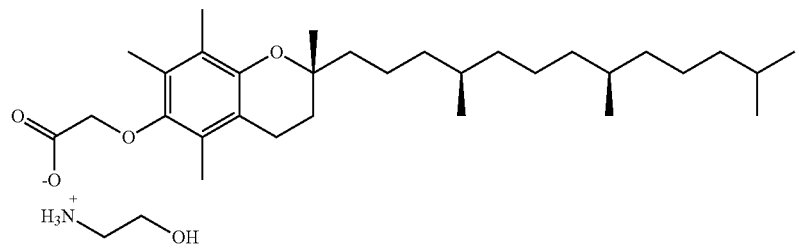

or a hydrate, thereof. In some embodiments, the compound is present as a polymorphic form having an X-ray powder diffraction pattern (CuKα) comprising a peak at about 19.4°2θ or a hydrate, thereof. In some embodiments, the X-ray powder diffraction pattern (CuKα) further comprises peaks at about 10.4, 14.1, and 17.8°2θ. In some embodiments, the X-ray powder diffraction pattern (CuKα) further comprises two peaks at about 20.8°2θ. In some embodiments, the polymorphic form has an X-ray powder diffraction pattern (CuKα) that is substantially as shown in FIG. 2. In some embodiments, the polymorphic form has a differential scanning calorimetry (DSC) isotherm comprising five endotherms from about 85° C. to about 97° C., from about 97° C. to about 105° C., from about 110° C. to about 125° C., from about 145° C. to about 155° C. and from about 160° C. to about 210° C. In some embodiments, the polymorphic form has a differential scanning calorimetry (DSC) isotherm comprising five endotherms at about 90.1° C., at about 100.7° C., at about 117.9° C., at about 149.7° C., and at about 181.6° C., respectively. In some embodiments, the polymorphic form has a differential scanning calorimetry isotherm that is substantially as shown in FIG. 3. In some embodiments, the polymorphic form has a thermogravimetric curve from thermogravimetric analysis (TGA) indicating a total volatile content of about 0.4 wt % over the temperature range of about 25-95.5° C.

In another embodiment, the present disclosure provides a compound of the formula:

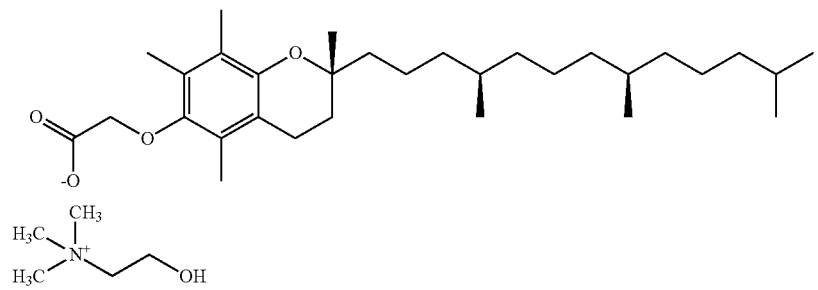

or a hydrate, thereof. In some embodiments, the compound is present as a polymorphic form having an X-ray powder diffraction pattern (CuKα) comprising two peaks at about 18.40 and 19.77°2θ or hydrate, thereof. In some embodiments, the polymorphic form has an X-ray powder diffraction pattern (CuKα) further comprising peaks at about 4.28 and 10.75°2θ. In some embodiments, the polymorphic form has an X-ray powder diffraction pattern (CuKα) further comprising two peaks at about 19.00°2θ. In some embodiments, the polymorphic form has an X-ray powder diffraction pattern (CuKα) further comprising 1, 2, 3, 4, 5, 6, 7, 8, 9, 10, 11, 12, 13, 14, 15, 16, 17, or all of peaks at about 6.45, 12.90, 16.17, 16.73, 17.31, 17.72, 20.96, 21.72, 28.08, 28.71, 29.70, 31.05, 31.63, 32.25, 34.60, 35.18, 36.60, and 39.02°2θ. In some embodiments, the polymorphic form has an X-ray powder diffraction pattern (CuKα) that is substantially as shown in FIG. 8. In some embodiments, the polymorphic form has a differential scanning calorimetry (DSC) isotherm comprising three endotherms from about 50° C. to about 60° C., from about 75° C. to about 85° C., and from about 150° C. to about 250° C., respectively. In some embodiments, the polymorphic form has a differential scanning calorimetry (DSC) isotherm comprising three endotherms at about 50° C., at about 80° C., and at about 150° C., respectively. In some embodiments, the polymorphic form has a differential scanning calorimetry isotherm that is substantially as shown in FIG. 9. In some embodiments, the polymorphic form has a thermogravimetric curve from thermogravimetric analysis (TGA) indicating a total volatile content of about 2.5 wt % over the temperature range of about 25-188.2° C.

In another embodiment, the present disclosure provides a compound of the formula:

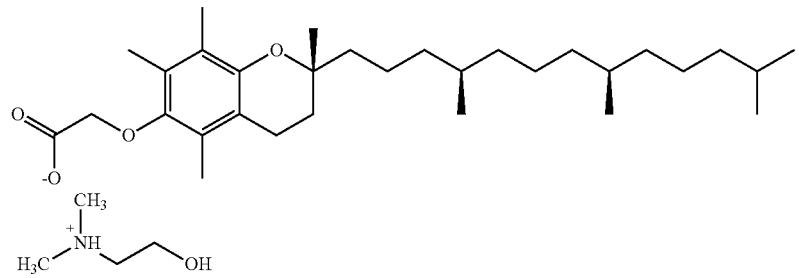

or a hydrate, thereof. In some embodiments, the compound is present as a polymorphic form having an X-ray powder diffraction pattern (CuKα) comprising a peak at about 21.73°2θ or a hydrate, thereof. In some embodiments, the polymorphic form has an X-ray powder diffraction pattern (CuKα) further comprising peaks at about 9.34, 14.90, 16.06, 17.33, 18.51, and 22.94°2θ. In some embodiments, the polymorphic form has an X-ray powder diffraction pattern (CuKα) further comprising two peaks centered at about 20.22°2θ. In some embodiments, the polymorphic form has an X-ray powder diffraction pattern (CuKα) further comprising 1, 2, 3, 4, 5, 6, 7, 8, 9, 10, 11, or all of peaks at about 10.05, 11.19, 14.13, 24.04, 27.65, 28.14, 29.73, 30.30, 31.06, 32.02, 33.45, and 34.49°2θ. In some embodiments, the polymorphic form has an X-ray powder diffraction pattern (CuKα) that is substantially as shown in FIG. 12. In some embodiments, the polymorphic form has a differential scanning calorimetry (DSC) isotherm comprising three endotherms from about 45° C. to about 55° C., from about 65° C. to about 80° C., and from about 80° C. to about 95° C. In some embodiments, the polymorphic form has a differential scanning calorimetry (DSC) isotherm comprising three endotherms at about 47° C., at about 73° C., and at about 87° C., respectively. In some embodiments, the polymorphic form has a differential scanning calorimetry isotherm that is substantially as shown in FIG. 13. In some embodiments, the polymorphic form has a thermogravimetric curve from thermogravimetric analysis (TGA) indicating a total volatile content of about 7.7 wt % over the temperature range of about 25-207° C.

In another aspect, the present disclosure provides a pharmaceutical composition comprising a compound, salt, or polymorphic form of the present disclosure and an excipient. In some embodiments, the pharmaceutical composition is formulated for administration: orally, intraadiposally, intraarterially, intraarticularly, intracranially, intradermally, intralesionally, intramuscularly, intranasally, intraocularly, intrapericardially, intraperitoneally, intrapleurally, intraprostatically, intrarectally, intrathecally, intratracheally, intratumorally, intraumbilically, intravaginally, intravenously, intravesicularlly, intravitreally, liposomally, locally, mucosally, parenterally, rectally, subconjunctival, subcutaneously, sublingually, topically, transbuccally, transdermally, vaginally, in crèmes, in lipid compositions, via a catheter, via a lavage, via continuous infusion, via infusion, via inhalation, via injection, via local delivery, or via localized perfusion. In some embodiments, the pharmaceutical composition is formulated for oral, intraarterial, intravenous, intraperitoneal, topical, or inhalational administration.

In yet another aspect, the present disclosure provides a method of reacting a compound of the formula:

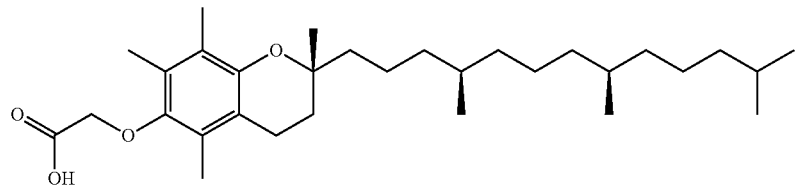 [SMILES: Cc1c(C)c2c(c(C)c1OCC(=O)O)CC[C@@](C)(CCC[C@H](C)CCC[C@H](C)CCCC(C)C)O2]

to obtain a polymorphic form comprising combining an about equal molar amount of a base and the compound in an alcoholic solvent and mixing for a time period from about 1 to about 24 hours. In some embodiments, the base is NaOH, KOH,

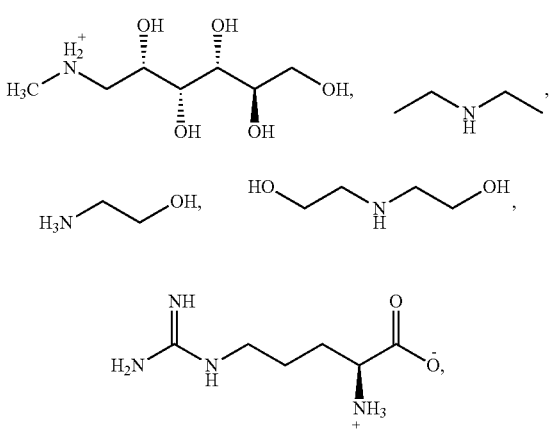

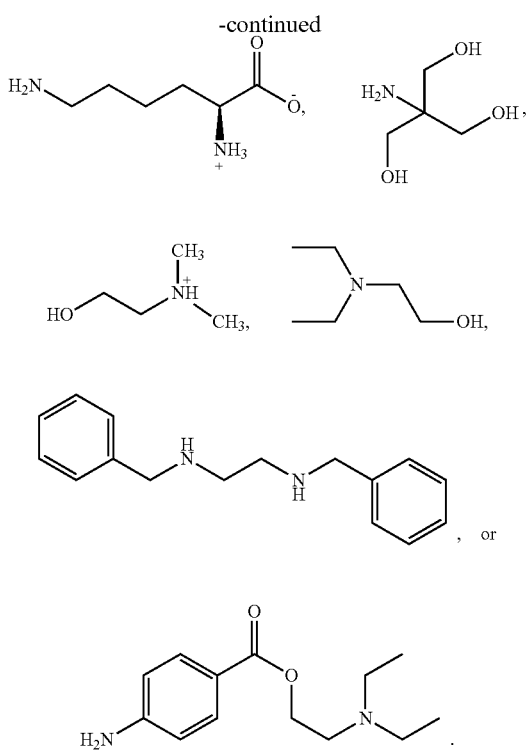

In some embodiments, the base is:

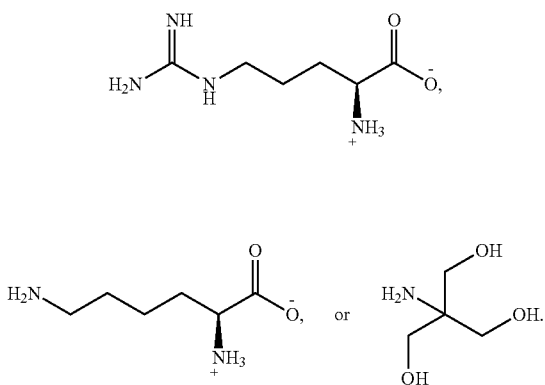

In some embodiments, the alcoholic solvent is of the formula: HO—$R_1$, wherein $R_1$ is alkyl$_{(C \leq 6)}$. In some embodiments, the alcoholic solvent is methanol, 1-butanol, or isopropyl alcohol. In some embodiments, the alcoholic solvent is isopropyl alcohol. In some embodiments, the method further comprises allowing the solution to slowly evaporate at room temperature. In some embodiments, the method further comprises allowing the evaporation to occur under a constant flow of nitrogen gas. In some embodiments, the constant flow of nitrogen has a pressure of about 2 psi.

In still another aspect, the present invention provides a method of treating or preventing a hyperproliferative disease, comprising administering to the patient a therapeutically effective amount of the pharmaceutical composition, salt, polymorphic form, or compound of the present disclosure. In some embodiments, the hyperproliferative disease is a cancer. In some embodiments, the cancer is breast cancer, lung cancer, colon cancer, an endometrial tumor, cervical cancer, ovarian cancer, mammary cancer, prostate cancer, liver cancer, melanoma, lymphoma, or myeloma. In some embodiments, the cancer is breast cancer. In some embodiments, the method further comprises administering to the patient a second therapy. In some embodiments, the second therapy is an immunotherapy or surgery. In some embodiments, the second therapy is an immunotherapy. In some embodiments, the immunotherapy comprises administering a pharmaceutically effective amount of trastuzumab, adoptively transferred T lymphocytes, or a therapeutic antibody. In some embodiments, the therapeutic antibody selectively binds HER2/neu. In some embodiments, the immunotherapy is trastuzumab. In some embodiments, the immunotherapy comprises administering adoptively transferred T lymphocytes to the patient. In some embodiments, the adoptively transferred T lymphocytes are engineered to express a chimeric antigen receptor (CAR) to the patient. In some embodiments, the immunotherapy comprises administering an immune modulating antibody to the patient. In some embodiments, the immune modulating antibody is an anti-PD-1, anti-4-1-BB, anti-GITR, anti-TIM3, anti-LAG3, anti-TIGIT, anti-CTLA-4 or an anti-LIGHT antibody. In other embodiments, the second therapy is radiotherapy or a chemotherapeutic agent. In other embodiments, the second therapy is surgery. In other embodiments, the second therapy is a chemotherapeutic agent. In some embodiments, the chemotherapeutic agent is anthracyclines, taxanes, methotrexate, mitoxantrone, estramustine, doxorubicin, etoposide, vinblastine, carboplatin, vinorelbine, 5-fluorouracil, cisplatin, topotecan, ifosfamide, cyclophosphamide, epirubicin, gemcitabine, vinorelbine, irinotecan, etoposide, vinblastine, pemetrexed, melphalan, capecitabine, oxaliplatin, BRAF inhibitors, and TGF-beta inhibitors.

In another aspect, the present disclosure provides a method of making a salt of the formula:

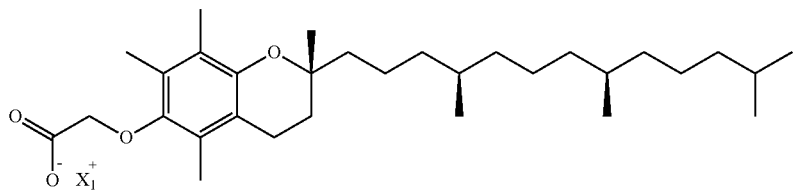

wherein: $X_1^+$ is a protonated base; comprising reacting a compound of the formula:

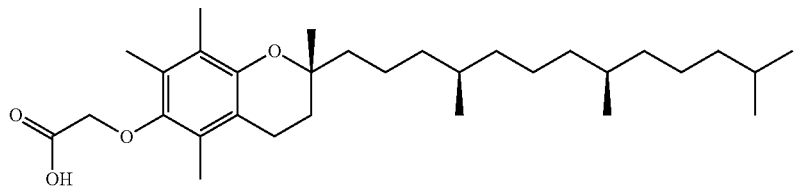 [SMILES: Cc1c(C)c2c(c(C)c1OCC(=O)O)CC[C@@](C)(CCC[C@H](C)CCC[C@H](C)CCCC(C)C)O2]

with the base sufficient to form a salt; or a hydrate thereof. In some embodiments, the base is: sodium hydroxide, potassium hydroxide, magnesium hydroxide, meglumine, diethylamine, ethanolamine, diethanolamine, L-arginine, L-lysine, choline, tris-hydroxymethylamine, N,N-dimethylethanolamine, 2-diethylethanolamine, calcium hydroxide, dibenzylethylenediamine, or procaine; or a hydrate thereof. In some embodiments, the base is ethanolamine, L-arginine, L-lysine, choline, tris-hydoxymethylamine, or N,N-dimethylethanolamine. In some embodiments, the base is L-arginine, L-lysine, or tris-hydroxymethylamine.

Other objects, features and advantages of the present disclosure will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description. Note that simply because a particular compound is ascribed to one particular generic formula does not mean that it cannot also belong to another generic formula.

BRIEF DESCRIPTION OF THE DRAWINGS

The following drawings form part of the present specification and are included to further demonstrate certain aspects of the present disclosure. The invention may be better understood by reference to one of these drawings in combination with the detailed description of specific embodiments presented herein.

DESCRIPTION OF ILLUSTRATIVE EMBODIMENTS

Figure 1:
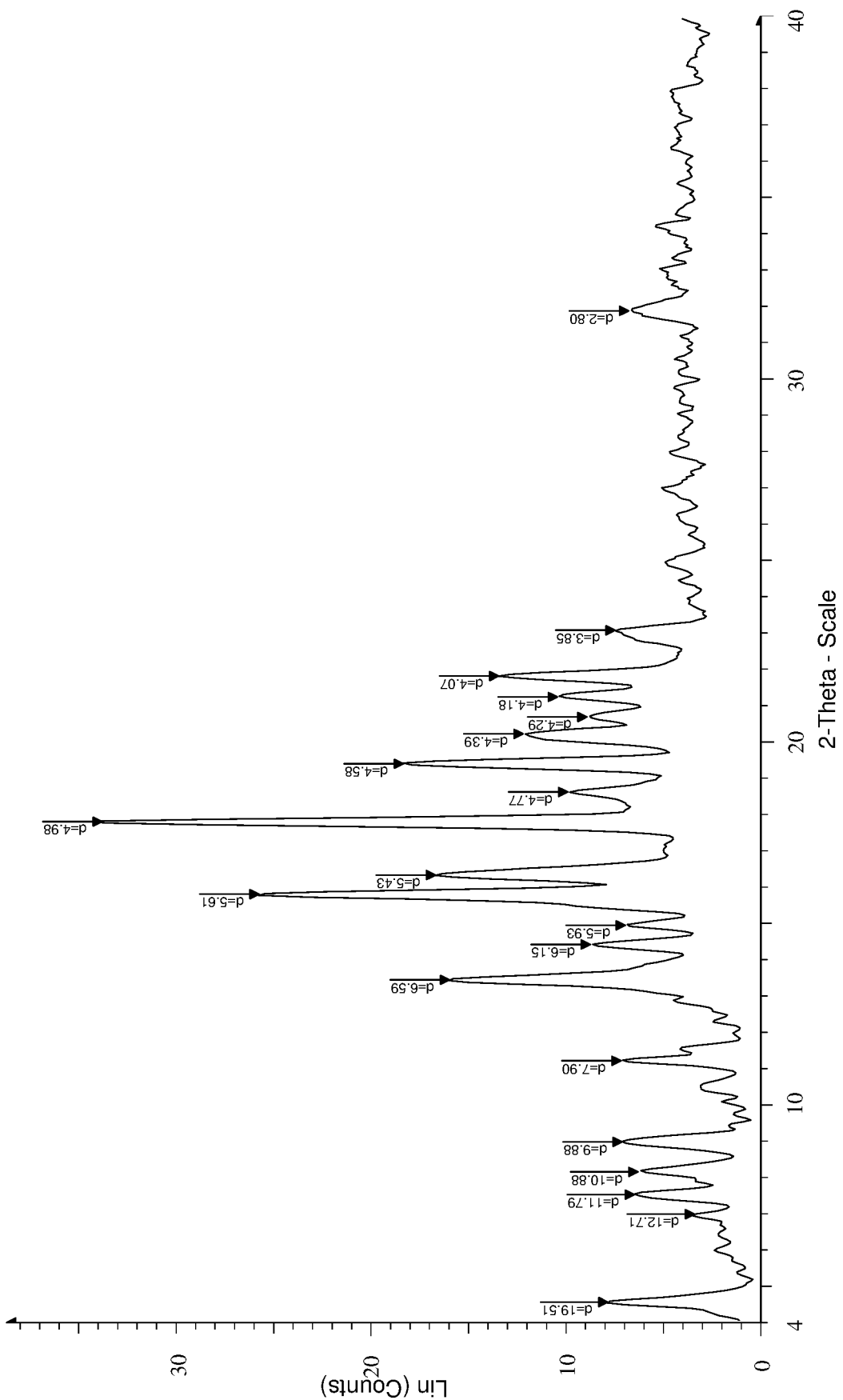
FIG. 1—The CuKα powder x-ray diffractogram of the α-TEA free acid. The diffractogram shows the dominate peaks of the free acid to be about 17.78° 2θ.

The present disclosure provides in one aspect, salts of the compound:

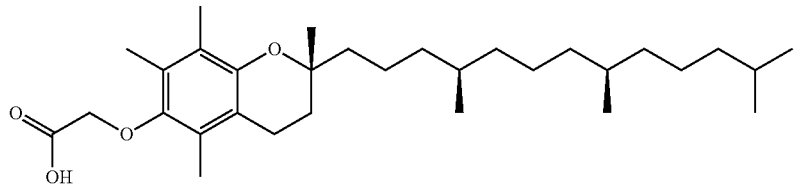 [SMILES: Cc1c(C)c2c(c(C)c1OCC(=O)O)CC[C@@](C)(CCC[C@H](C)CCC[C@H](C)CCCC(C)C)O2]

and polymorphic forms of the compound, thereof. In another non-limiting example, the present disclosure relates to pharmaceutical compositions of the polymorphic forms and the method of preparation of these compounds and the method of use of these compounds to treat diseases.

I. Definitions

When used in the context of a chemical group: "hydrogen" means —H; "hydroxy" means —OH; "oxo" means =O; "carboxylic acid", "carboxy", or "carboxyl" means —C(=O)OH (also written as —COOH or —CO$_2$H); "carboxylate" means —C(=O)O$^-$ (also written as —COO$^-$ or —CO$_2^-$); "halo" means independently —F, —Cl, —Br or —I. Any undefined valency on an atom of a structure shown in this application implicitly represents a hydrogen atom bonded to the atom.

In the context of chemical formulas, the symbol "—" means a single bond, "=" means a double bond; and "≡" means triple bond. The symbol "◂▬▬" means a single bond where the group attached to the thick end of the wedge is "out of the page." The symbol "▪▫▫▫▫" means a single bond where the group attached to the thick end of the wedge is "into the page". The symbol "∿∿" means a single bond where the conformation (e.g., either R or S) or the geometry is undefined (e.g., either E or Z).

For the groups and classes below, the following parenthetical subscripts further define the group/class as follows: "(Cn)" defines the exact number (n) of carbon atoms in the group/class. "(C≤n)" defines the maximum number (n) of carbon atoms that can be in the group/class, with the minimum number as small as possible for the group in question, e.g., "alkyl$_{(C≤8)}$" For example, "alkyl$_{(C≤10)}$" designates those alkyl groups having from 1 to 10 carbon atoms (e.g., 1, 2, 3, 4, 5, 6, 7, 8, 9, or 10, or any range derivable therein (e.g., 3 to 10 carbon atoms). (Cn-n') defines both the minimum (n) and maximum number (n') of carbon atoms in the group. Similarly, "alkyl$_{(C2-10)}$" designates those alkyl groups having from 2 to 10 carbon atoms (e.g., 2, 3, 4, 5, 6, 7, 8, 9, or 10, or any range derivable therein (e.g., 3 to 10 carbon atoms)).

The term "saturated" as used herein means the compound or group so modified has no carbon-carbon double and no carbon-carbon triple bonds, except as noted below. The term does not preclude carbon-heteroatom multiple bonds, for example a carbon oxygen double bond or a carbon nitrogen double bond. Moreover, it does not preclude a carbon-carbon double bond that may occur as part of keto-enol tautomerism or imine/enamine tautomerism.

The term "aliphatic" when used without the "substituted" modifier signifies that the compound/group so modified is an acyclic or cyclic, but non-aromatic hydrocarbon compound or group. In aliphatic compounds/groups, the carbon atoms can be joined together in straight chains, branched chains, or non-aromatic rings (alicyclic). Aliphatic compounds/groups can be saturated, that is joined by single bonds (alkanes/alkyl), or unsaturated, with one or more double bonds (alkenes/alkenyl) or with one or more triple bonds (alkynes/alkynyl). When the term "aliphatic" is used without the "substituted" modifier only carbon and hydrogen atoms are present. When the term is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$, —OC(O)CH$_3$, or —S(O)$_2$NH$_2$.

The term "alkyl" when used without the "substituted" modifier refers to a monovalent saturated aliphatic group with a carbon atom as the point of attachment, a linear or branched, cyclo, cyclic or acyclic structure, and no atoms other than carbon and hydrogen. Thus, as used herein cycloalkyl is a subset of alkyl. The groups —CH$_3$ (Me), —CH$_2$CH$_3$ (Et), —CH$_2$CH$_2$CH$_3$ (n-Pr), —CH(CH$_3$)$_2$(iso-Pr), —CH(CH$_2$)$_2$(cyclopropyl), —CH$_2$CH$_2$CH$_2$CH$_3$ (n-Bu), —CH(CH$_3$)CH$_2$CH$_3$ (sec-butyl), —CH$_2$CH(CH$_3$)$_2$(iso-butyl), —C(CH$_3$)$_3$(tert-butyl), —CH$_2$C(CH$_3$)$_3$(neo-pentyl), cyclobutyl, cyclopentyl, cyclohexyl, and cyclohexylmethyl are non-limiting examples of alkyl groups. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$, —OC(O)CH$_3$, or —S(O)$_2$NH$_2$. The following groups are non-limiting examples of substituted alkyl groups: —CH$_2$OH, —CH$_2$Cl, —CF$_3$, —CH$_2$CN, —CH$_2$C(O)OH, —CH$_2$C(O)OCH$_3$, —CH$_2$C(O)NH$_2$, —CH$_2$C(O)CH$_3$, —CH$_2$OCH$_3$, —CH$_2$OC(O)CH$_3$, —CH$_2$NH$_2$, —CH$_2$N(CH$_3$)$_2$, and —CH$_2$CH$_2$Cl. An "alkane" refers to the compound H—R, wherein R is alkyl. The term "alcohol" is an alkane as that term is defined herein wherein one or more of the hydrogen atoms have been replaced with a hydroxyl group.

The term "heteroaryl" when used without the "substituted" modifier refers to a monovalent aromatic group with an aromatic carbon atom or nitrogen atom as the point of attachment, said carbon atom or nitrogen atom forming part of one or more aromatic ring structures wherein at least one of the ring atoms is nitrogen, oxygen or sulfur, and wherein the heteroaryl group consists of no atoms other than carbon, hydrogen, aromatic nitrogen, aromatic oxygen and aromatic sulfur. If more than one ring is present, the rings may be fused or unfused. As used herein, the term does not preclude the presence of one or more alkyl, aryl, and/or aralkyl groups (carbon number limitation permitting) attached to the aromatic ring or aromatic ring system. Non-limiting examples of heteroaryl groups include furanyl, imidazolyl, indolyl, indazolyl (Im), isoxazolyl, methylpyridinyl, oxazolyl, phenylpyridinyl, pyridinyl, pyrrolyl, pyrimidinyl, pyrazinyl, quinolyl, quinazolyl, quinoxalinyl, triazinyl, tetrazolyl, thiazolyl, thienyl, and triazolyl. The term "N-heteroaryl" refers to a heteroaryl group with a nitrogen atom as the point of attachment. A "heteroarene" refers to the compound H—R, wherein R is heteroaryl. Pyridine and quinoline are non-limiting examples of heteroarenes. When these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$.

The term "heterocycloalkyl" when used without the "substituted" modifier refers to a monovalent non-aromatic group with a carbon atom or nitrogen atom as the point of attachment, said carbon atom or nitrogen atom forming part of one or more non-aromatic ring structures wherein at least one of the ring atoms is nitrogen, oxygen or sulfur, and wherein the heterocycloalkyl group consists of no atoms other than carbon, hydrogen, nitrogen, oxygen and sulfur. If more than one ring is present, the rings may be fused or unfused. As used herein, the term does not preclude the presence of one or more alkyl groups (carbon number limitation permitting) attached to the ring or ring system. Also, the term does not preclude the presence of one or more double bonds in the ring or ring system, provided that the resulting group remains non-aromatic. Non-limiting examples of heterocycloalkyl groups include aziridinyl, azetidinyl, pyrrolidinyl, piperidinyl, piperazinyl, morpholinyl, thiomorpholinyl, tetrahydrofuranyl, tetrahydrothiofuranyl, tetrahydropyranyl, pyranyl, oxiranyl, and oxetanyl. The term "N-heterocycloalkyl" refers to a heterocycloalkyl group with a nitrogen atom as the point of attachment. When these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, —S(O)$_2$NH$_2$, or —C(O)OC(CH$_3$)$_3$(tert-butyloxycarbonyl, BOC).

The term "alkylamino" when used without the "substituted" modifier refers to the group —NHR, in which R is an alkyl, as that term is defined above. Non-limiting examples include: —NHCH$_3$ and —NHCH$_2$CH$_3$. The term "dialkylamino" when used without the "substituted" modifier refers to the group —NRR', in which R and R' can be the same or different alkyl groups. Non-limiting examples of dialkylamino groups include: —N(CH$_3$)$_2$ and —N(CH$_3$)(CH$_2$CH$_3$). Similarly, a trialkylamino is the group —RR'R" in which R, R', and R" can be the same or different alkyl groups. Non-limiting examples of dialkylamino groups include: —N(CH$_3$)$_3$$^+$ and —N(CH$_3$)$_2$(CH$_2$CH$_3$)$^+$. Furthermore, a trialkylamino group forms a positive charge when bonded to another compound. When any of these terms is used with the "substituted" modifier one or more hydrogen atom attached to a carbon atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$.

The use of the word "a" or "an," when used in conjunction with the term "comprising" in the claims and/or the specification may mean "one," but it is also consistent with the meaning of "one or more," "at least one," and "one or more than one."

Throughout this application, the term "about" is used to indicate that a value includes the inherent variation of error for the device, the method being employed to determine the value, or the variation that exists among the study subjects. When used in the context of X-ray powder diffraction, the terms "about" and "substantially" are used interchangeably to indicate a value of ±0.5°2θ from the reported value, preferably a value of ±0.2°2θ from the reported value. When used in the context of differential scanning calorimetry, thermogravimetric analysis, or glass transition temperatures, the terms "about" and "substantially" are used interchangeably to indicate a value of ±10° C. relative to the maximum of the peak, preferably a value of ±2° C. relative to the maximum of the peak.

The term "base" when used in the context of this application represents a compound which contains a group which contains a group which has a lone pair of electrons or a highly polarized and labile bond such as a metal alkane like butyllithium or a Gringard reagent. Such bases can form a positively charged compound which interacts with the negatively charged carboxylate to form a "salt". In some embodiments, the base is a nitrogenous base which contains a nitrogen atom with a lone pair of electrons which can act as a traditional Lewis base. Such nitrogenous bases is a compound which contains at least one amino, alkylamino, dialkylamino, trialkylamino, or a heteroaryl or heterocycloalkyl group which contains at least one nitrogen atom. In some embodiments, the base can be a substituted version of these compounds wherein the substituted version comprises a compound wherein at least one hydrogen atom has been replaced with —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$, —OC(O)CH$_3$, or —S(O)$_2$NH$_2$.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps.

The term "effective," as that term is used in the specification and/or claims, means adequate to accomplish a desired, expected, or intended result. "Effective amount," "Therapeutically effective amount" or "pharmaceutically effective amount" when used in the context of treating a patient or subject with a compound means that amount of the compound which, when administered to a subject or patient for treating a disease, is sufficient to effect such treatment for the disease.

The term "hydrate" when used as a modifier to a compound means that the compound has less than one (e.g., hemihydrate), one (e.g., monohydrate), or more than one (e.g., dihydrate) water molecules associated with each compound molecule, such as in solid forms of the compound.

As used herein, the term "IC$_{50}$" refers to an inhibitory dose which is 50% of the maximum response obtained. This quantitative measure indicates how much of a particular drug or other substance (inhibitor) is needed to inhibit a given biological, biochemical or chemical process (or component of a process, i.e. an enzyme, cell, cell receptor or microorganism) by half.

An "isomer" of a first compound is a separate compound in which each molecule contains the same constituent atoms as the first compound, but where the configuration of those atoms in three dimensions differs.

As used herein, the term "patient" or "subject" refers to a living mammalian organism, such as a human, monkey, cow, horse, sheep, goat, dog, cat, mouse, rat, guinea pig, or transgenic species thereof. In certain embodiments, the patient or subject is a primate. Non-limiting examples of human subjects are adults, juveniles, infants and fetuses.

As generally used herein "pharmaceutically acceptable" refers to those compounds, materials, compositions, and/or dosage forms which are, within the scope of sound medical judgment, suitable for use in contact with the tissues, organs, and/or bodily fluids of human beings and animals without excessive toxicity, irritation, allergic response, or other problems or complications commensurate with a reasonable benefit/risk ratio.

"Prevention" or "preventing" includes: (1) inhibiting the onset of a disease in a subject or patient which may be at risk and/or predisposed to the disease but does not yet experience or display any or all of the pathology or symptomatology of the disease, and/or (2) slowing the onset of the pathology or symptomatology of a disease in a subject or patient which may be at risk and/or predisposed to the disease but does not yet experience or display any or all of the pathology or symptomatology of the disease.

A "stereoisomer" or "optical isomer" is an isomer of a given compound in which the same atoms are bonded to the same other atoms, but where the configuration of those atoms in three dimensions differs. "Enantiomers" are stereoisomers of a given compound that are mirror images of each other, like left and right hands. "Diastereomers" are stereoisomers of a given compound that are not enantiomers. Chiral molecules contain a chiral center, also referred to as a stereocenter or stereogenic center, which is any point, though not necessarily an atom, in a molecule bearing groups such that an interchanging of any two groups leads to a stereoisomer. In organic compounds, the chiral center is typically a carbon, phosphorus or sulfur atom, though it is also possible for other atoms to be stereocenters in organic and inorganic compounds. A molecule can have multiple stereocenters, giving it many stereoisomers. In compounds whose stereoisomerism is due to tetrahedral stereogenic centers (e.g., tetrahedral carbon), the total number of hypothetically possible stereoisomers will not exceed $2^n$, where n is the number of tetrahedral stereocenters. Molecules with symmetry frequently have fewer than the maximum possible number of stereoisomers. A 50:50 mixture of enantiomers is referred to as a racemic mixture. Alternatively, a mixture of enantiomers can be enantiomerically enriched so that one enantiomer is present in an amount greater than 50%. Typically, enantiomers and/or diastereomers can be resolved or separated using techniques known in the art. It is contemplated that that for any stereocenter or axis of chirality for which stereochemistry has not been defined, that stereocenter or axis of chirality can be present in its R form, S form, or as a mixture of the R and S forms, including racemic and non-racemic mixtures. As used herein, the phrase "substantially free from other stereoisomers" means that the composition contains ≤15%, more preferably ≤10%, even more preferably ≤5%, or most preferably ≤1% of another stereoisomer(s).

"Treatment" or "treating" includes (1) inhibiting a disease in a subject or patient experiencing or displaying the pathology or symptomatology of the disease (e.g., arresting further development of the pathology and/or symptomatology), (2) ameliorating a disease in a subject or patient that is experiencing or displaying the pathology or symptomatology of the disease (e.g., reversing the pathology and/or symptomatology), and/or (3) effecting any measurable decrease in a disease in a subject or patient that is experiencing or displaying the pathology or symptomatology of the disease.

The above definitions supersede any conflicting definition in any of the reference that is incorporated by reference herein. The fact that certain terms are defined, however, should not be considered as indicative that any term that is undefined is indefinite. Rather, all terms used are believed to describe the invention in terms such that one of ordinary skill can appreciate the scope and practice the present invention.

II. Salts of α-TEA and Synthetic Methods

While the compound has shown improved efficacy in treating such tumors, α-TEA has proven difficult to formulate into a commercially successful drug given its liquid crystal like nature and ability to deform easily when manipulated. In order to overcome this challenge, in some embodiments, the present disclosure describes attempts to synthesize a salt of α-TEA using a variety of different bases which exhibit improved properties than α-TEA. During the development of the present disclosure, 16 potential bases were examined. Of the bases, 6 formed crystalline salts which showed improved characteristics over the free acid of α-TEA. The three α-TEA salts, the salts of lysine, arginine, and tris, were isolated and studied in detail. These three salts exhibited improved physical properties over the free acid without any loss of activity.

Salts of α-TEA can be prepared according to the methods described in the Examples section below. These methods can be further modified and optimized using the principles and techniques of organic chemistry as applied by a person skilled in the art. Such principles and techniques are taught, for example, in *March's Advanced Organic Chemistry: Reactions, Mechanisms, and Structure* (2007), which is incorporated by reference herein.

The salts of α-TEA may contain one or more asymmetrically-substituted carbon or nitrogen atoms, and may be isolated in optically active or racemic form. Thus, all chiral, diastereomeric, racemic form, epimeric form, and all geometric isomeric forms of a structure are intended, unless the specific stereochemistry or isomeric form is specifically indicated. The salts of α-TEA may occur as racemates and racemic mixtures, single enantiomers, diastereomeric mixtures and individual diastereomers. In some embodiments, a single diastereomer is obtained. The chiral centers of the present invention can have the S or the R configuration.

In addition, atoms making up the salts of α-TEA of the present invention are intended to include all isotopic forms of such atoms. Isotopes, as used herein, include those atoms having the same atomic number but different mass numbers. By way of general example and without limitation, isotopes of hydrogen include tritium and deuterium, and isotopes of carbon include $^{13}C$ and $^{14}C$. Similarly, it is contemplated that one or more carbon atom(s) of a compound of the present invention may be replaced by a silicon atom(s). Furthermore, it is contemplated that one or more oxygen atom(s) of the salts of α-TEA may be replaced by a sulfur or selenium atom(s).

The salts of α-TEA and polymorphic form thereof may also have the advantage that they may be more efficacious than, be less toxic than, be longer acting than, be more potent than, produce fewer side effects than, be more easily absorbed than, and/or have a better pharmacokinetic profile (e.g., higher oral bioavailability and/or lower clearance) than, and/or have other useful pharmacological, physical, or chemical advantages over, compounds known in the prior art for use in the indications stated herein.

III. Hyperproliferative Diseases

Hyperproliferative diseases generally include any disease which causes a cell to begin to reproduce uncontrollably such as, e.g., cancer. In cancer, the cell's normal apoptotic cycle is interrupted and thus agents that can induce apoptosis in the cell can be important therapeutic agents for treating these diseases. α-TEA compounds have been shown to lead to cellular apoptosis and as such can potentially be used to treat a variety of types of cancer lines. As such, the salts of α-TEA and the polymorphic forms thereof may be used as effective treatments for cancers such as an endometrial tumor, mammary cancer, lung cancer, ovarian cancer, prostate cancer, breast cancer, cervical cancer, liver cancer, colon cancer, lymphoma, or melanoma. In various aspects, it is anticipated that salts and polymorphic forms of the present invention may be used to treat virtually any malignancy.

The compounds and polymorphic forms may be used to treat cancer cells including but are not limited to cells from the bladder, blood, bone, bone marrow, brain, breast, colon, esophagus, gastrointestine, gum, head, kidney, liver, lung, nasopharynx, neck, ovary, prostate, skin, stomach, pancreas, testis, tongue, cervix, or uterus. In addition, the cancer may specifically be used with the following histological type, though it is not limited to these: neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; branchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; androblastoma, malignant; sertoli cell carcinoma; leydig cell tumor, malignant; lipid cell tumor, malignant; paraganglioma, malignant; extramammary paraganglioma, malignant; pheochromocytoma; glomangiosarcoma; malignant melanoma; amelanotic melanoma; superficial spreading melanoma; malig melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; mullerian mixed tumor; nephroblastoma; hepatoblastoma; carcinosarcoma; mesenchymoma, malignant; brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; mesonephroma, malignant; hemangiosarcoma; hemangioendothelioma, malignant; kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; hodgkin's disease; hodgkin's; paragranuloma; malignant lymphoma, small lymphocytic; malignant lymphoma, large cell, diffuse; malignant lymphoma, follicular; mycosis fungoides; other specified non-hodgkin's lymphomas; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; and hairy cell leukemia. In certain aspects, the tumor comprises an osteosarcoma, angiosarcoma, rhabdosarcoma, leiomyosarcoma, Ewing sarcoma, glioblastoma, neuroblastoma, or leukemia.

IV. Pharmaceutical Formulations and Routes of Administration

For administration to a mammal in need of such treatment, the salts of α-TEA in a therapeutically effective amount may be used in combination with one or more excipients appropriate to the indicated route of administration. The salts of α-TEA may be used when admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia, sodium alginate, polyvinylpyrrolidone, and/or polyvinyl alcohol, and tableted or encapsulated for convenient administration. Alternatively, the salts of α-TEA may be dissolved in water, polyethylene glycol, propylene glycol, ethanol, corn oil, cottonseed oil, peanut oil, sesame oil, benzyl alcohol, sodium chloride, and/or various buffers. Other excipients and modes of administration are well and widely known in the pharmaceutical art.

In some embodiments, the pharmaceutical compositions useful in the present disclosure can be subjected to conventional pharmaceutical operations such as sterilization and/or contain conventional pharmaceutical carriers and excipients such as preservatives, stabilizers, wetting agents, emulsifiers, buffers, etc.

In some embodiments, the salts of α-TEA are administered by a variety of methods, e.g., orally or by injection (e.g. subcutaneous, intravenous, intraperitoneal, etc.). Depending on the route of administration, the active salts of α-TEA may be coated in a material to protect the compound from the action of acids and other natural conditions which may inactivate the compound. They may also be administered by continuous perfusion/infusion of a disease or wound site.

To administer the therapeutic compound by other than parenteral administration, in some embodiments, it can be necessary to coat the salts of α-TEA with, or co-administer the salts of α-TEA with, a material to prevent its inactivation. For example, the therapeutic compound may be administered to a patient in an appropriate carrier, for example, liposomes, or a diluent. Pharmaceutically acceptable diluents include saline and aqueous buffer solutions. Liposomes include water-in-oil-in-water CGF emulsions as well as conventional liposomes.

In some embodiments, the therapeutic salts of α-TEA are also administered parenterally, intraperitoneally, intraspinally, or intracerebrally. Dispersions can be prepared in glycerol, liquid polyethylene glycols, and mixtures thereof and in oils. Under ordinary conditions of storage and use, these preparations can contain, in some embodiments, a preservative to prevent the growth of microorganisms.

Pharmaceutical compositions suitable for injectable use include sterile aqueous solutions (where water soluble) or dispersions and sterile powders for the extemporaneous preparation of sterile injectable solutions or dispersion are also envisioned. In all cases, the composition must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (such as, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, sodium chloride, or polyalcohols such as mannitol and sorbitol, in the composition. Prolonged absorption of the injectable compositions can be brought about by including in the composition an agent which delays absorption, for example, aluminum monostearate or gelatin.

Sterile injectable solutions can be prepared by incorporating the therapeutic salts of α-TEA in the required amount in an appropriate solvent with one or a combination of ingredients enumerated above, as required, followed by filtered sterilization. Generally, dispersions are prepared by incorporating the therapeutic compound into a sterile carrier which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient (i.e., the therapeutic compound) plus any additional desired ingredient from a previously sterile-filtered solution thereof.

The therapeutic salts of α-TEA can be orally administered, for example, with an inert diluent or an assimilable edible carrier. The therapeutic compound and other ingredients may also be enclosed in a hard or soft shell gelatin capsule, compressed into tablets, or incorporated directly into the subject's diet. For oral therapeutic administration, the therapeutic salts of α-TEA may be used with excipients and used in the form of ingestible tablets, buccal tablets, troches, capsules, elixirs, suspensions, syrups, wafers, and the like. The percentage of the therapeutic compound in the compositions and preparations may, of course, be varied. The amount of the therapeutic salts of α-TEA in such therapeutically useful compositions is such that a suitable dosage will be obtained.

It is especially advantageous to formulate parenteral compositions in dosage unit form for ease of administration and uniformity of dosage. Dosage unit form as used herein refers to physically discrete units suited as unitary dosages for the subjects to be treated; each unit containing a predetermined quantity of therapeutic salts of α-TEA calculated to produce the desired therapeutic effect in association with the required pharmaceutical carrier. The specification for the dosage unit forms of the invention are dictated by and directly dependent on (a) the unique characteristics of the therapeutic salts of α-TEA and the particular therapeutic effect to be achieved, and (b) the limitations inherent in the art of compounding such a therapeutic compound for the treatment of a selected condition in a patient.

The therapeutic compound may also be administered topically to the skin, eye, or mucosa. Alternatively, if local delivery to the lungs is desired the therapeutic compound may be administered by inhalation in a dry-powder or aerosol formulation.

Active salts of α-TEA are administered at a therapeutically effective dosage sufficient to treat a condition associated with a condition in a patient. For example, the efficacy of the salts of α-TEA can be evaluated in an animal model system that may be predictive of efficacy in treating the disease in humans, such as the model systems shown in the examples and drawings.

The actual dosage amount of the salts of α-TEA of the present disclosure or composition comprising the salts of α-TEA of the present disclosure administered to a subject may be determined by physical and physiological factors such as age, sex, body weight, severity of condition, the type of disease being treated, previous or concurrent therapeutic interventions, idiopathy of the subject and on the route of administration. These factors may be determined by a skilled artisan. The practitioner responsible for administration will typically determine the concentration of active ingredient(s) in a composition and appropriate dose(s) for the individual subject. The dosage may be adjusted by the individual physician in the event of any complication.

An effective amount typically will vary from about 2 mg/kg to about 50 mg/kg, in one or more dose administrations daily, for one or several days (depending of course of the mode of administration and the factors discussed above). In some particular embodiments, the amount is less than 5,000 mg per day with a range of 100 mg to 4500 mg per day.

The effective amount may be less than 10 mg/kg/day, less than 100 mg/kg/day, less than 250 mg/kg/day, less than 100 mg/kg/day, less than 50 mg/kg/day, less than 25 mg/kg/day or less than 10 mg/kg/day. It may alternatively be in the range of 1 mg/kg/day to 200 mg/kg/day.

In other non-limiting examples, a dose also comprises from about 10 mg/kg/body weight, about 100 mg/kg/body weight, about 10 g/kg/body weight, about 5 g/kg/body weight, or more per administration, and any range derivable therein. In non-limiting examples of a derivable range from the numbers listed herein, a range of about 1 mg/kg/body weight to about 100 mg/kg/body weight, about 5 g/kg/body weight to about 10 g/kg/body weight, etc., can be administered, based on the numbers described above.

In certain embodiments, a pharmaceutical composition of the present disclosure comprises, for example, at least about 0.1% of a salt of α-TEA described in the present disclosure. In other embodiments, the compound of the present disclosure comprises between about 0.25% to about 75% of the weight of the unit, or between about 25% to about 60%, or between about 1% to about 10%, for example, and any range derivable therein.

Single or multiple doses of the agents are contemplated. Desired time intervals for delivery of multiple doses can be determined by one of ordinary skill in the art employing no more than routine experimentation. As an example, subjects may be administered two doses daily at approximately 12 hour intervals. In some embodiments, the agent is administered once a day.

The salts of α-TEA may be administered on a routine schedule. As used herein a routine schedule refers to a predetermined designated period of time. The routine schedule may encompass periods of time which are identical or which differ in length, as long as the schedule is predetermined. For instance, the routine schedule may involve administration twice a day, every day, every two days, every three days, every four days, every five days, every six days, a weekly basis, a monthly basis or any set number of days or weeks there-between. Alternatively, the predetermined routine schedule may involve administration on a twice daily basis for the first week, followed by a daily basis for several months, etc. In other embodiments, the disclosure provides that the agent(s) can be taken orally and that the timing of which is or is not dependent upon food intake. Thus, for example, the agent can be taken every morning and/or every evening, regardless of when the subject has eaten or will eat. In other embodiments, the disclosure is taken as a dietary supplement. In some embodiments, the α-TEA salts are taken before the onset of the tumor as a prophylaxis measure. In other embodiments, the α-TEA salts are taken as a treatment option for use as an antiproliferative agent.

V. Combination Therapy

In addition to being used as a monotherapy, the salts of α-TEA described in the present invention may also find use in combination therapies. Effective combination therapy may be achieved with a single composition or pharmacological formulation that includes both agents, or with two distinct compositions or formulations, administered at the same time, wherein one composition includes a salt of α-TEA, and the other includes the second agent(s). The other therapeutic modality may be administered before, concurrently with, or following administration of the salts or polymorphic forms of α-TEA. The therapy using the salts or polymorphic forms of α-TEA may precede or follow administration of the other agent(s) by intervals ranging from minutes to weeks. In embodiments where the other agent and the salts or polymorphic forms of α-TEA are administered separately, one would generally ensure that a significant period of time did not expire between the time of each delivery, such that each agent would still be able to exert an advantageously combined effect. In such instances, it is contemplated that one would typically administer the salts or polymorphic forms of α-TEA and the other therapeutic agent within about 12-24 hours of each other and, more preferably, within about 6-12 hours of each other, with a delay time of only about 12 hours being most preferred. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations.

It also is conceivable that more than one administration of a salt or polymorphic form of α-TEA, or the other agent will be desired. In this regard, various combinations may be employed. By way of illustration, where the salts or polymorphic forms of α-TEA is "A" and the other agent is "B", the following permutations based on 3 and 4 total administrations are exemplary:

A/B/A  B/A/B  B/B/A  A/A/B  B/A/A  A/B/B  B/B/B/A  B/B/A/B
A/A/B/B  A/B/A/B  A/B/B/A  B/B/A/A  B/A/B/A  B/A/A/B  B/B/B/A
A/A/A/B  B/A/A/A  A/B/A/A  A/A/B/A  A/B/B/B  B/A/B/B  B/B/A/B

Other combinations are likewise contemplated. Non-limiting examples of pharmacological agents that may be used in the present invention include any pharmacological agent known to be of benefit in the treatment of a cancer or hyperproliferative disorder or disease. In some embodiments, combinations of the salts or polymorphic forms of α-TEA with a cancer targeting immunotherapy, radiotherapy, chemotherapy, or surgery are contemplated. Also contemplated is a combination of a salt or polymorphic form of α-TEA with more than one of the above mentioned methods including more than one type of a specific therapy. In some embodiments, it is contemplated that the immunotherapy is a monoclonal antibody which targets HER2/neu such trastuzumab (Herceptin®) or a similar antibody. In other embodiments, the immunotherapy can be other cancer targeting antibodies such as alemtuzumab (Campath®), bevacizumab (Avastin®), cetuximab (Eribitux®), and panitumumab (Vectibix®) or conjugated antibodies such as ibritumomab tiuxetan (Zevalin®), tositumomab (Bexxar®), brentuximab vedotin (Adcetris®), ado-trastuzumab emtansine (Kadcyla™), or denileukin dititox (Ontak®) as well as immune cell targeting antibodies such as ipilimumab (Yervoy®), tremelimumab, anti-PD-1, anti-4-1-BB, anti-GITR, anti-TIM3, anti-LAG-3, anti-TIGIT, anti-CTLA-4, or anti-LIGHT. Furthermore, in some embodiments, the salts or polymorphic forms of α-TEA are envisioned to be used in combination therapies with dendritic cell-based immunotherapies such as Sipuleucel-T (Provenge®) or adoptive T-cell immunotherapies.

Furthermore, it is contemplated that the salts or polymorphic forms of α-TEA are used in combination with a chemotherapeutic agent such as anthracyclines, taxanes, methotrexate, mitoxantrone, estramustine, doxorubicin, etoposide, vinblastine, carboplatin, vinorelbine, 5-fluorouracil, cisplatin, topotecan, ifosfamide, cyclophosphamide, epirubicin, gemcitabine, vinorelbine, irinotecan, etoposide, vinblastine, pemetrexed, melphalan, capecitabine, oxaliplatin, BRAF inhibitors, and TGF-beta inhibitors. In some embodiments, the combination therapy is designed to target a cancer such as those listed above. In the preferred embodiments, the cancer the combination therapy is designed to treat is an endometrial tumor, mammary cancer, lung cancer, ovarian cancer, prostate cancer, breast cancer, cervical cancer or colon cancer.

VI. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

A. Methods

1. Microscopy

A Zeiss Universal microscope configured with a polarized visible light source and polarizable analyzer was used to evaluate the optical properties of the samples. Specimens were typically mounted on a microscope slide with a cover glass. Because of the "waxy" nature of the material slide preparations were manually smeared with a spatula and appearance noted. Observations of particle/crystal size and shape and birefringence were recorded.

2. Hot Stage Microscopy (HSM)

A Linkam hot stage accessory was used in tandem with the microscope. Specimens were mounted on a microscope slide with a cover glass. Samples were heated from room temperature through melting using a Linkam TMS 94 temperature control and Linksys 32 data capture software system. Observations of possible phase change, melting, recrystallization, decomposition, etc. were recorded.

3. Proton Nuclear Magnetic Resonance ($^1$H NMR)

Samples were analyzed by 1H NMR to determine stoichiometry (molar ratio of acid to base counter ion). Spectra of salt candidates were compared to that of the free acid and changes in chemical shifts indicating salt formation observed. Samples were prepared by dissolving in a chloroform:methanol:water mixture with 0.05% (v/v) tetramethylsilane (TMS). Spectra were collected at ambient temperature on a Bruker Avance III 400 MHz FT-NMR spectrometer and Bruker Topspin software (version 2.1). Prior to each sample analysis, the magnetic field surrounding the sample was optimized by an automated shimming program.

4. Differential Scanning Calorimetry (DSC)

Differential scanning calorimetry (DSC) is a technique used to measure characteristic heat flux of a test article as it is scanned through a temperature gradient under a controlled atmosphere. Thermal phase transitions such as endothermic melting and exothermic decomposition were recorded. DSC data were collected on a TA Instruments DSC. In general, samples in the mass range of 1 to 10 mg were crimped in aluminum sample pans and scanned from 25 to approximately 300° C. at 10° C./min using a nitrogen purge of 50 mL/min.

5. Thermogravimetric Analysis (TGA)

Thermogravimetric analysis involves the determination of the mass of a specimen as a function of temperature. TGA data were collected on a TA Instruments Q500 TGA. In general, samples in the mass range of 2 to 10 mg were placed in an open, pre-tared platinum sample pan and attached by fine wire to a microbalance. The sample was suspended into a furnace which was heated from 25 to about 250° C. at 10° C./min using a nitrogen purge at 100 mL/min. Sample weight change as a function of temperature was observed.

6. X-Ray Powder Diffraction (XRD)

X-ray powder diffraction patterns were obtained using a Bruker D8 Discovery diffractometer equipped with an XYZ stage, laser video microscope for positioning, and a two dimensional HiStar area Detector or a scintillation detector. A CuKα radiation 1.5406 angstrom source operating at 40 kV and 40 mA was used to irradiate samples. The X-ray optics consists of a Gobel mirror coupled with a pinhole collimator of 0.5 or 1.0 mm. Theta-theta continuous scans were employed with a sample-detector distance of approximately 30 cm, which gives an effective 2θ range of 4-40° C. Samples were mounted in low background quartz plates.

7. Solubility

Milligram size (2 mg) quantities of each sample were placed into a vial. Buffered water (pH 4, 7, and 10) was added and the vials were stirred for a few minutes, followed by visual observation for remaining solids. The solvent was incrementally added until the solids were dissolved, or a maximum volume of solvent (10 mL) was added and the experiment was terminated.

8. Hygroscopicity—Dynamic Vapor Sorption (DVS)

DVS is a gravimetric screening technique that measures how quickly and how much of a solvent (water) is adsorbed by a sample. The relative humidity or vapor concentration surrounding the sample is varied while the change in mass of the sample is measured. A vapor sorption isotherm shows the equilibrium amount of vapor sorbed as a function of relativity humidity. The mass values at each relative humidity step are used to generate the isotherm. Isotherms are divided in two components: sorption for increasing humidity steps and desorption for decreasing humidity steps. A plot of kinetic data is also supplied which shows the change in mass and humidity as a function of time.

Samples were analyzed using a TA Q2000 automated dynamic vapor sorption analyzer. The samples were dried at 40° C. for 5 hours and then cooled to 25° C. with a dry nitrogen purge over them until they no longer lost mass at 0% RH. The samples were then subjected to 0 to 95% RH, back to 0% RH at 25° C. in 5% RH steps.

9. Stability

The scaled up salts and free acid were challenged by heat (solids stored at 25 and 60° C. for 1 week), oxidation (solids stored in oxygen headspace at 25° C. for 1 week), light (solids exposed≥1×ICH International Conference on Harmonization of Technical Requirements for Registration of Pharmaceuticals for Human Use UV confirmatory conditions), and solutions (HPLC diluent-methanol) at 25 and 40° C. for 1 week.

These samples were analyzed, along with unstressed controls, by HPLC to characterize their stability.

10. HPLC Analysis

Salt candidates were analyzed by total area normalization (TAN). The samples were dissolved in methanol at a concentration of 0.8 mg/mL.

HPLC Conditions

HPLC Column: Sunfire C18, 3.5 μm, 4.6×150 mm
Column Temp: 45° C.
Autosampler Flush: 25:75 Acetonitrile:reagent alcohol
Flow Rate: 1.5 mL/min
Injection Volume: 10 μL
UV Detection: 215 nm
Mobile Phase: A—0.1% acetic acid in acetonitrile
    B—0.1% acetic acid in reagent alcohol
Gradient Pump Program:

| Step Time (minutes) | % A | % B | Curve |
| --- | --- | --- | --- |
| 0.5 | 92.0 | 8.0 | 0.0 |
| 6.0 | 92.0 | 8.0 | 0.0 |
| 6.0 | 10.0 | 90.0 | 1.0 |
| 2.0 | 10.0 | 90.0 | 0.0 |
| 7.0 | 92.0 | 8.0 | 0.0 |

B. Salt Screen

1. Characterization of the Free Acid

The α-TEA free acid, lot 54543-7-34, was analyzed by XRD, DSC, TGA. DVS and microscopy. The sample is crystalline as shown by the XRD pattern in FIG. 1. The DSC thermogram of the free acid shows a melting endotherm onset at 54.5° C. The TGA thermogram shows the free acid to be free of volatiles, with a weight loss of 0.2% at 207.5° C.

DVS was performed on a sample of the free acid. The free acid exhibits a total weight gain of about 0.2 weight % at 95% RH. This data indicates that the free acid does not form hydrates or exhibit deliquescence.

The free acid was examined using optical microscopy. The sample exhibited areas of both birefringent and amorphous agglomerates. Manual manipulation of the sample under magnification resulted in a smearing and a droplet like appearance. This behavior suggests that the free acid has some of the characteristics of a liquid crystal. Liquid crystals are a state of matter that have properties between those of a conventional liquid and those of a solid. Liquid crystals are substances that are not as rigidly ordered as a solid, but have some degree of alignment. Molecules which tend to be candidates for having liquid crystal phases are often long having a rigid central region and end groups that are slightly flexible.

2. Primary Salt Screen (50 mg Scale) Preparative Procedures

The predicted $pK_a$ value of the α-TEA free acid is 3.23. Based on these predicated $pK_a$ values, a library of salt forming bases were chosen and is shown in Table 1.

TABLE 1

Salt Forming Bases

| Base | $pK_a$ | Class* |
|---|---|---|
| sodium hydroxide | 14 | I |
| potassium hydroxide | 14 | I |
| magnesium hydroxide | 11.4 | I |
| meglumine | 8 | I |
| diethylamine | 10.9 | II |
| ethanolamine | 9.5 | III |
| diethanolamine | 9.3 | III |
| L-Arginine | 13.2 | I |
| L-Lysine | 10.8 | I |
| Choline | >11 | I |
| tris-hydroxymethylamine (Tris) | 8 | II |
| deanol, N,N-dimethylethanolamine | 8.8 | II |
| 2-diethylaminoethanol | 9.6 | II |
| calcium hydroxide | 12.6 | I |
| Benzathine, dibenzylethylenediamine | 9.99 | II |
| procaine | 8.9 | II |

*Safety and pharmaceutical acceptability of the counter-ions: class I-unrestricted used based on physiological ubiquitous ions or intermediate metabolites; class II-universally approved, but not naturally occurring. Low toxicity and good tolerability; class III-case by case limited approval, some reactivity, some pharmacological activity.

Initially, a series of experiments consisted of 7 salts prepared on an approximately 50 mg scale were carried out and are panel 1. A solution of free acid was prepared in methanol and appropriate molar equivalents of base solution and/or solids were added. Samples were mixed several hours and allowed to slowly evaporate at room temperature with about 2 psi nitrogen purge.

Characterization of the resultant salts was performed using X-ray diffraction (XRD). One sample (ethanolamine) exhibited a crystalline pattern different than the free acid starting material indicating possible salt formation. The remaining six samples produced amorphous materials. These six samples were solvent ripened in an attempt to increase the crystallinity of the resultant salts. Unfortunately, this technique had limited successful in increasing the crystallinity.

The crystalline salt candidate, ethanolamine, was further characterized by differential scanning calorimetry (DSC). An overview of the results is summarized in Table 2.

TABLE 2

Panel 1

| Base | Class | Sample ID | Appearance | Crystallinity/XRD | DSC |
|---|---|---|---|---|---|
| sodium hydroxide | I | 116 | waxy solid | amorphous | N/A |
| potassium hydroxide | I | 117 | glassy[1] | amorphous | N/A |
| magnesium hydroxide | I | 118 | glassy[1] | amorphous | N/A |
| meglumine | I | 119 | waxy solid | amorphous | N/A |
| diethylamine | II | 120 | glassy[1] | amorphous | N/A |
| ethanolamine | III | 121 | waxy solid | crystalline possible salt | Multiple endotherms |
| diethanolamine | III | 122 | glassy[1] | amorphous | N/A |

[1]glassy materials are amorphous (not crystalline) non free flowing solids which often do not exhibit a sharp melting endotherm during DSC analysis.

The next group of experiments, panel 2, consists of 8 salts prepared on an approximately 50 mg scale. A solution of free acid was prepared in I-butanol and appropriate molar equivalents of base solution and or solids were added. Samples were mixed several hours and allowed to slowly evaporate at room temperature with about 2 psi nitrogen purge.

Characterization was performed using X-ray Diffraction (XRD). One sample (ethanolamine) exhibited a crystalline pattern similar to the pattern from Panel 1, indicating possible salt formation. Two samples exhibited evidence of the base counterion, which would indicate that no salt was formed. The remaining five samples produced amorphous materials. These five samples were solvent ripened in an attempt to increase the crystallinity. Again, this technique was not successful in increasing the crystallinity.

The results of Panel 2 are listed in Table 3.

TABLE 3

Panel 2

| Base | Class | Sample ID | Appearance | Crystallinity/XRD |
|---|---|---|---|---|
| sodium hydroxide | I | 412 | glassy | amorphous |
| potassium hydroxide | I | 413 | glassy | amorphous |
| magnesium hydroxide | I | 414 | waxy solid | no salt, evidence of MgOH |
| meglumine | I | 415 | waxy solid | amorphous |
| diethylamine | II | 416 | glassy | amorphous |
| ethanolamine | III | 417 | waxy solid | crystalline, possible salt |
| diethanolamine | III | 418 | glassy | amorphous |
| calcium hydroxide | I | 419 | waxy solid | Amorphous, no salt, evidence of Ca(OH)$_2$ |

Finally, another set of experiments, Panel 3, consisting of 16 salts was prepared on approximately 50 mg scale. A solution of free acid was prepared in isopropyl alcohol and appropriate molar equivalents of base solution and or solids were added. Samples were mixed several hours and allowed to slowly evaporate at room temperature with about 2 psi nitrogen purge.

Characterization was performed using XRD. Six samples (ethanolamine, arginine, lysine, choline, tris, and deanol) exhibited crystalline XRD patterns indicating possible salt formation. The eight remaining samples produced amorphous materials. These eight samples were solvent ripened in an attempt to increase the crystallinity. This technique was not successful in increasing the crystallinity. Two samples exhibited evidence of the base counter-ion, indicating that no salt formation.

The Panel 3 results are listed in Table 4.

TABLE 4

Panel 3

| Base | Class | Sample ID | Appearance | Crystallinity/XRD | DSC |
| --- | --- | --- | --- | --- | --- |
| sodium hydroxide | I | 510 | waxy solid | amorphous | N/A |
| potassium hydroxide | I | 511 | glassy | amorphous | N/A |
| magnesium hydroxide | I | 512 | waxy solid | no salt, evidence of MgOH | N/A |
| meglumine | I | 513 | waxy solid | amorphous | N/A |
| diethylamine | II | 514 | glassy | amorphous | N/A |
| ethanolamine | III | 515 | waxy solid | crystalline, possible salt | Multiple endotherms |
| diethanolamine | III | 516 | glassy | amorphous | N/A |
| L-arginine | I | 517 | solid | crystalline, possible salt | Multiple endotherms |
| L-lysine | I | 518 | solid | crystalline, possible salt | Multiple endotherms |
| choline | I | 519 | waxy solid | low crystallinity, possible salt | Multiple endotherms |
| Tris-hydroxyl-ethanolamine | II | 520 | waxy solid | low crystallinity, possible salt | Multiple endotherms |
| Deanol, N,N-dimethylethanolamine | II | 521 | waxy solid | crystalline, possible salt | Multiple endotherms |
| 2-diethylaminoethanol | I | 522 | glassy | amorphous | N/A |
| calcium hydroxide | I | 523 | white solid | no salt, evidence of Ca(OH)$_2$ | N/A |
| Benzathine, dibenzyl-ethylenediamine | II | 524 | glassy | amorphous | N/A |
| procaine | II | 525 | glassy | amorphous | N/A |

3. Primary Salt Screen (50 mg Scale) Results and Discussion

Panels 1 through 3 produced six crystalline salt compounds. The characteristics of these compounds are further described below.

a) Ethanolamine

Figure 2:
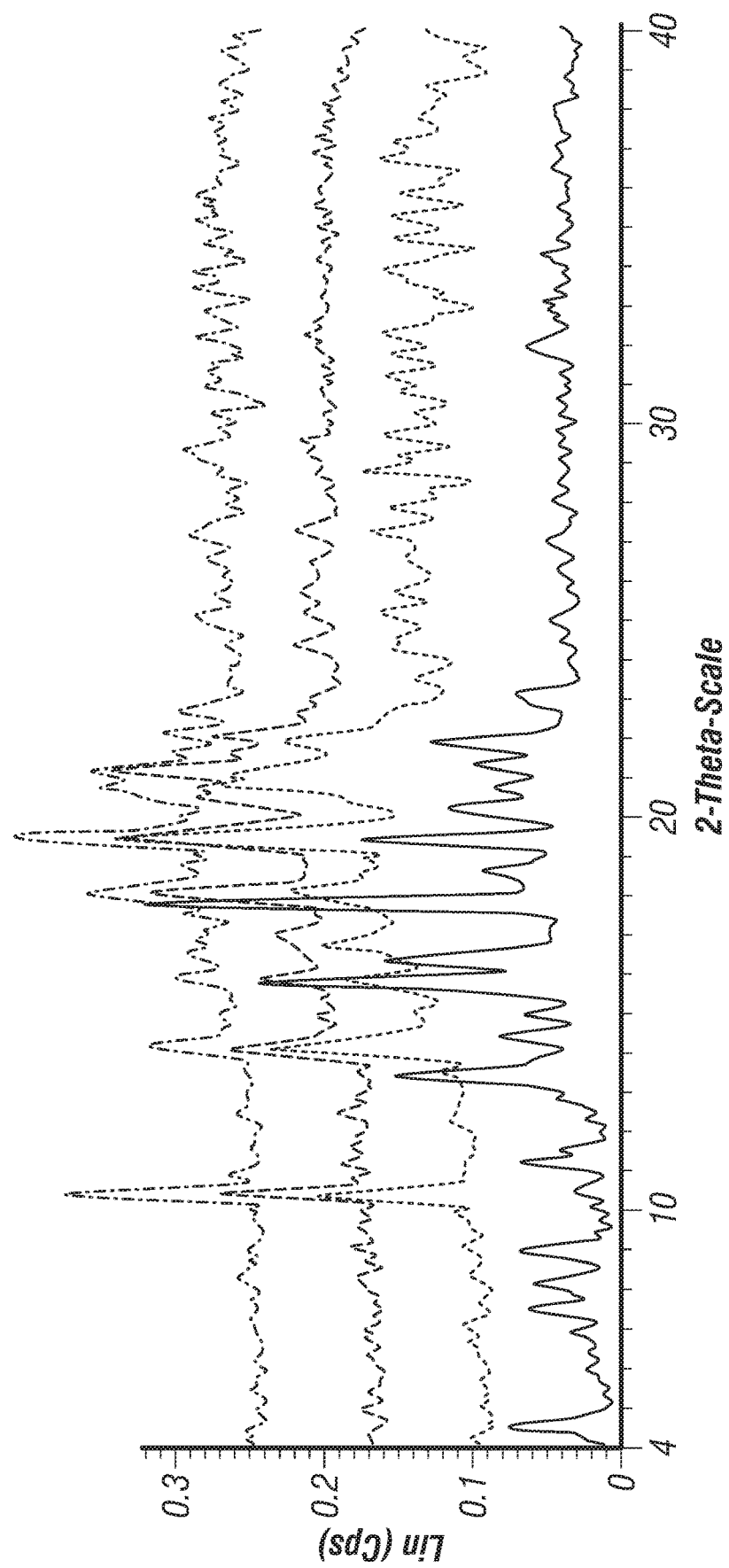
FIG. 2—A CuKα powder x-ray diffractogram of the ethanolamine salt candidates from panels 1-3 compared to the spectra of the α-TEA free acid. The spectra for the free acid is shown at the bottom, the ethanolamine salt from panel 2 is shown second from the bottom, the ethanolamine salt from panel 1 is shown in the second from the top spectra, and the ethanolamine salt from panel 3 is shown at the top.
Figure 3:
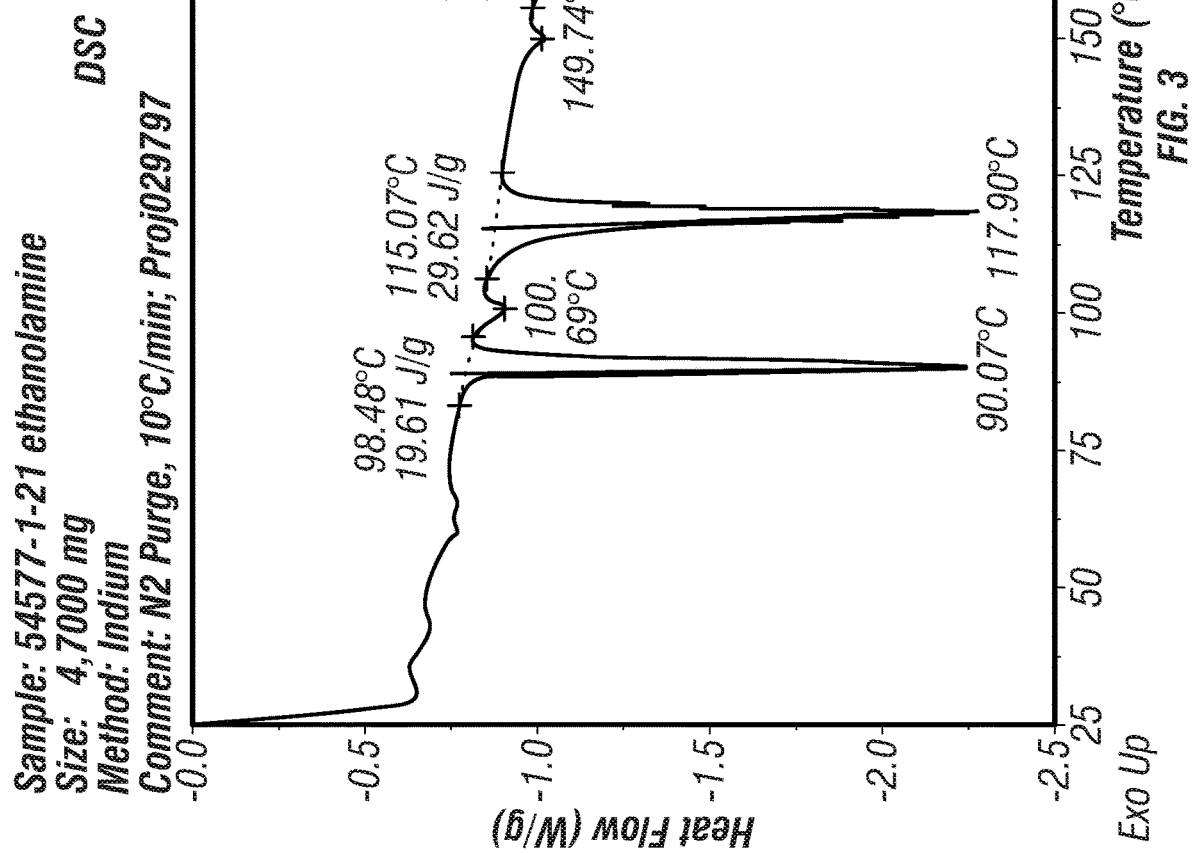
FIG. 3—A differential scanning calorimetry (DSC) isotherm of the ethanolamine salt candidate of the α-TEA free acid showing five endotherms with the three largest endotherms at about 90, 118, and 182° C.

The ethanolamine salt of α-TEA is a waxy crystalline solid. The unique X-ray diffraction characteristics were observed in all three panels and are shown in FIG. 2. The DSC thermogram exhibited multiple endothermic transitions with temperatures of about 88, 100, 115, 149 and 169° C. The DSC plot is shown in FIG. 3. The total volatile content by TGA over the temperature range 25-95.5° C. was 0.4 wt %.

The $^1$H NMR of this compound shows the stoichiometry of free acid to base to be in a 1:1 ratio. A change in chemical shifts from the free acid spectrum was observed suggesting the compound is a salt.

b) L-Arginine

Figure 4:
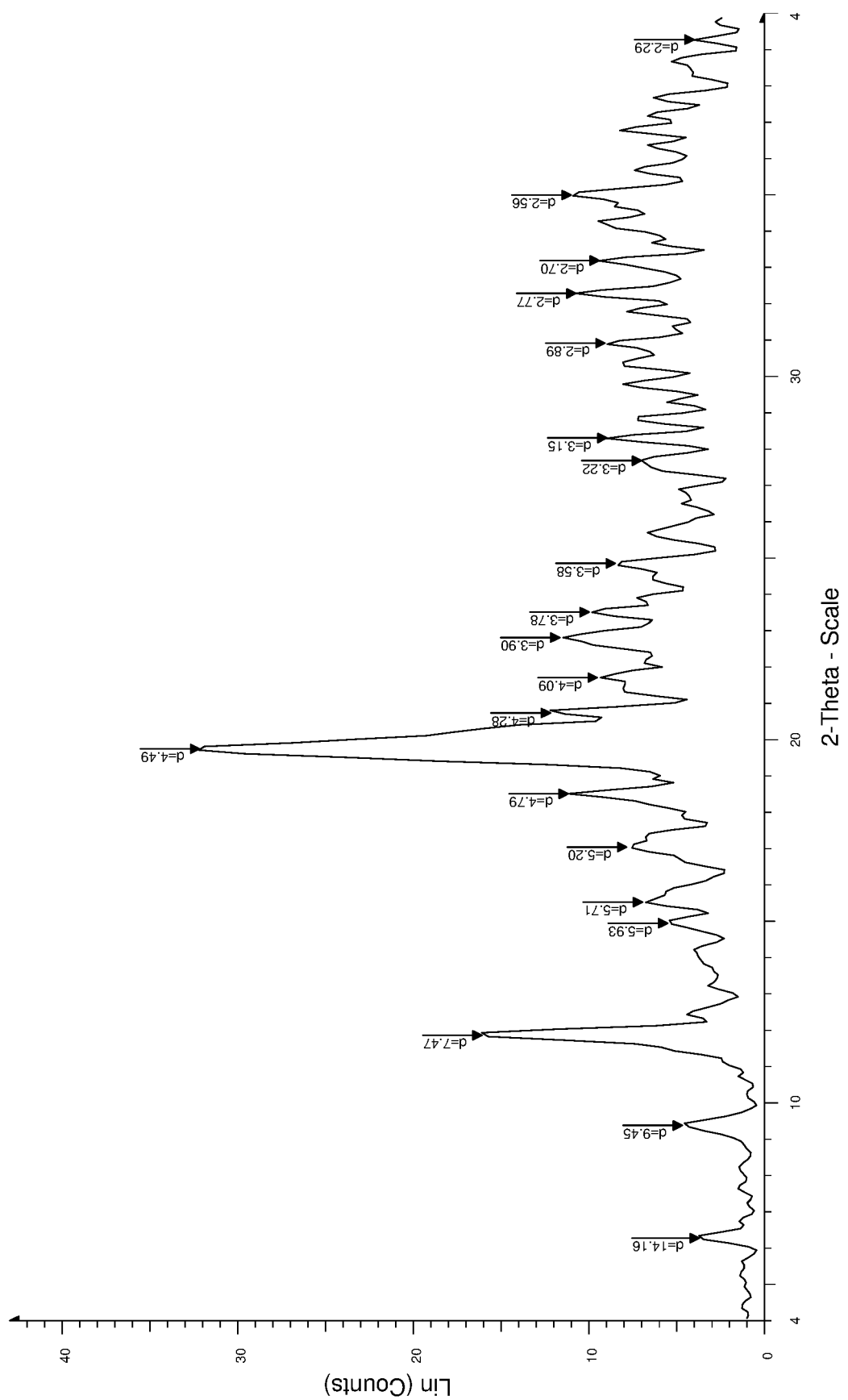
FIG. 4—A CuKα powder x-ray diffractogram of a representative arginine salt candidate from panels 1-3. The spectra shows a dominate peak at about 19.74°2θ.
Figure 5:
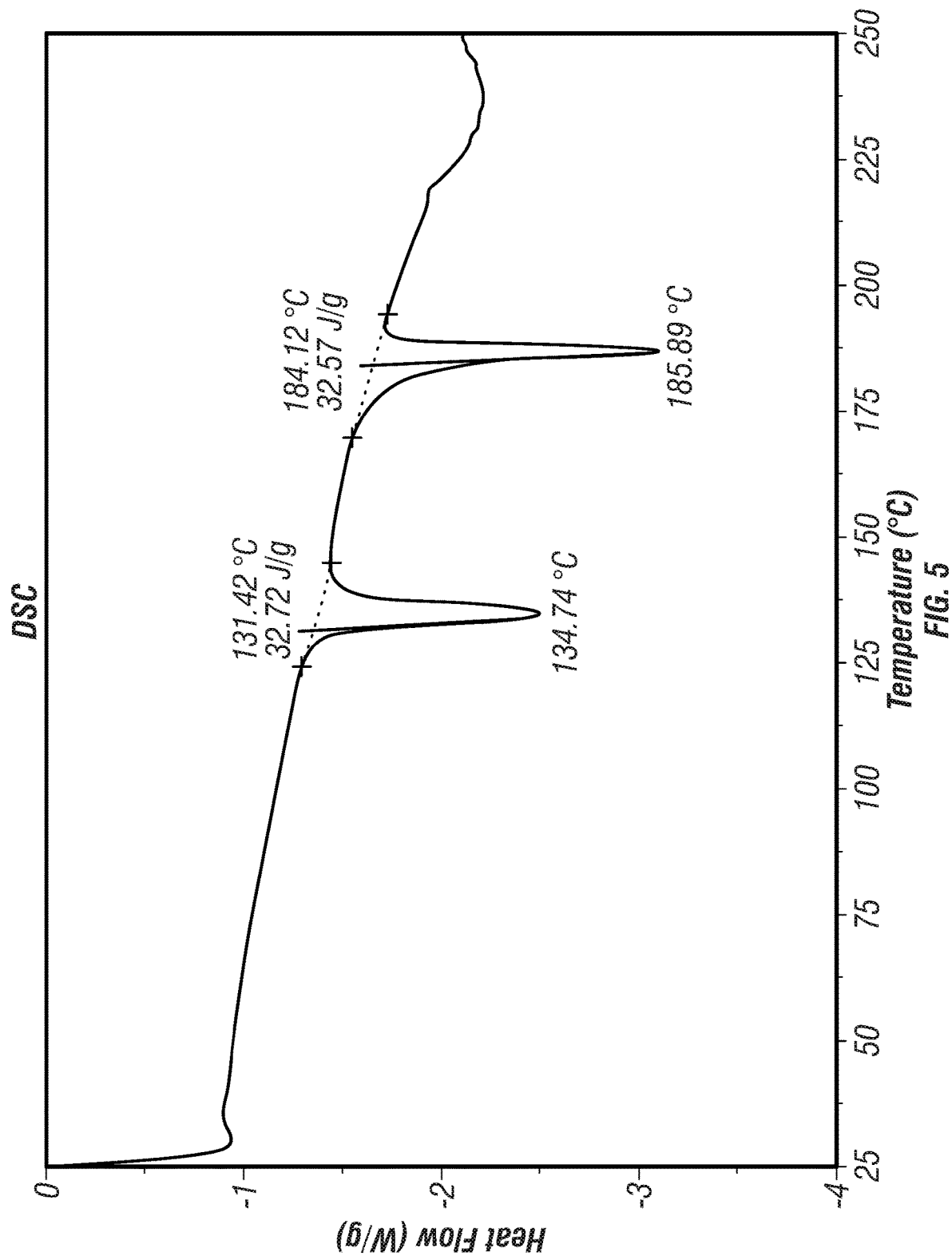
FIG. 5—A differential scanning calorimetry (DSC) isotherm of the arginine salt candidate of the α-TEA free acid showing two endotherms with the endotherms at about 131 and 184° C.

The arginine salt of α-TEA was a partially crystalline solid that was less "waxy" than the free acid. The unique X-ray diffraction pattern of the L-arginine sample is shown in FIG. 4. The DSC thermogram exhibited multiple endothermic transitions at about 131 and 184° C. The DSC plot is shown in FIG. 5. The total volatile content by TGA over the temperature range 25-194° C. was about 0.3 wt %.

The $^1$H NMR of this candidate shows the stoichiometry of free acid to base to be in a 1:1 ratio. A change in chemical shifts from the free acid spectrum was observed suggesting this candidate is a salt.

The dynamic vapor sorption (DVS) isotherm indicates a possible hemihydrate formation (1.3% weight gain) at about 40% RH. The desorption cycle indicates that the hydration process is reversible. The particle size of this material was very small as evidenced by photomicrograph. The salt produced some liquid crystal-like behavior, but to a lesser degree than observed with the free acid. The approximate visual solubility of the arginine salt in pH 4, 7, and 10 buffers was <0.2 mg/mL.

c) L-Lysine

Figure 6:
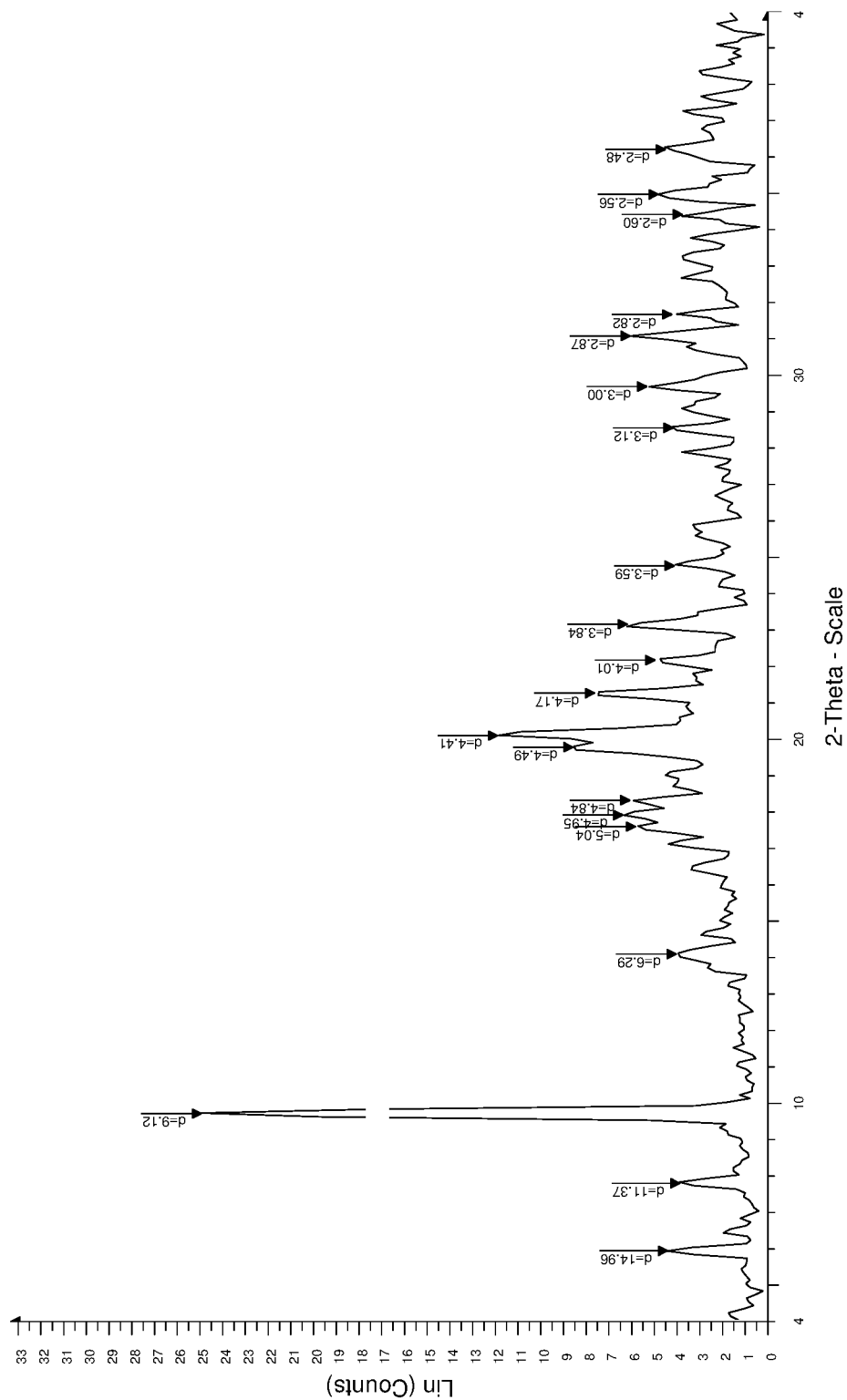
FIG. 6—A CuKα powder x-ray diffractogram of a representative lysine salt candidate. The spectra shows a dominate peak at about 9.69°2θ.
Figure 7:
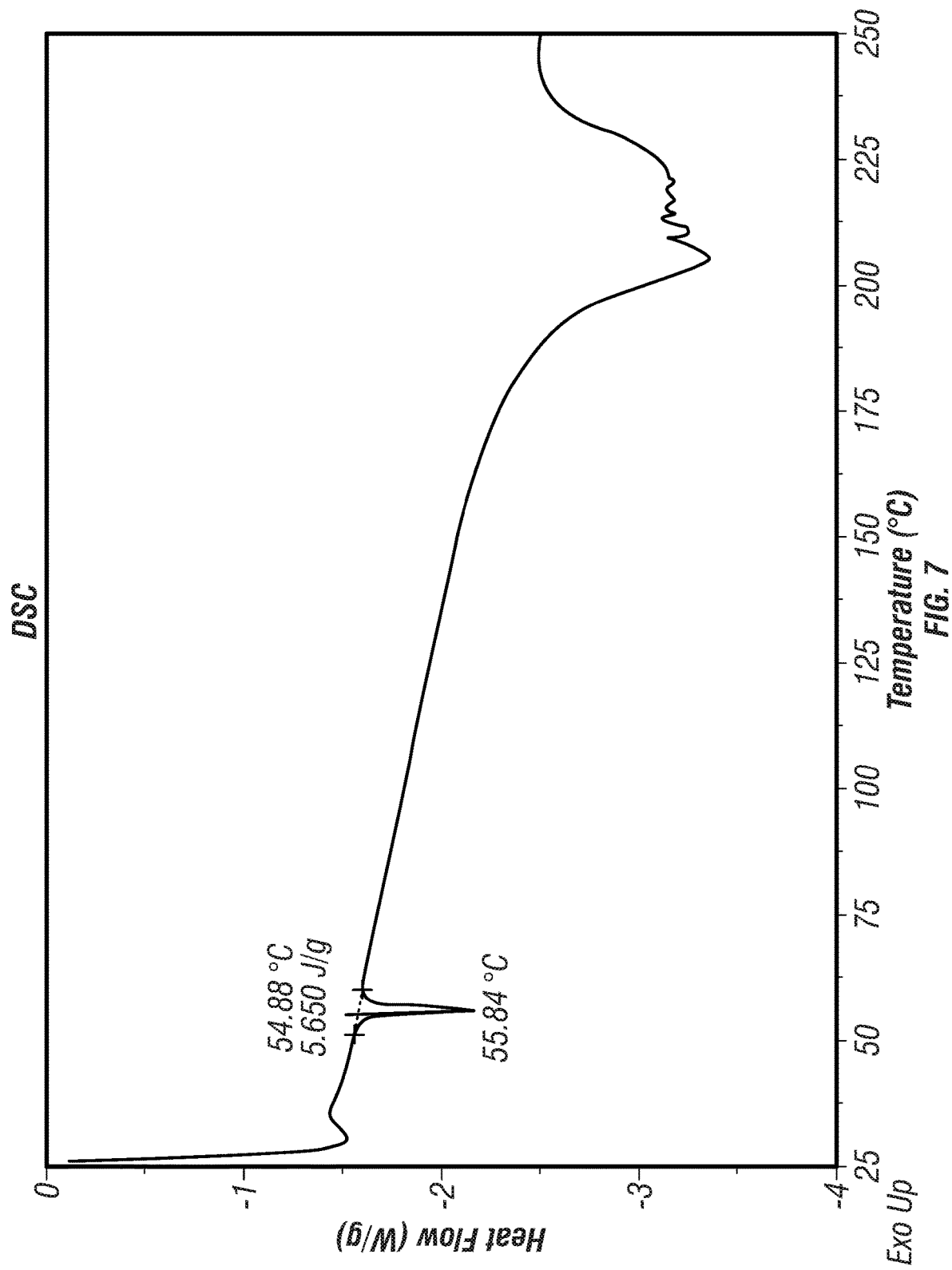
FIG. 7—A differential scanning calorimetry (DSC) isotherm of the lysine salt candidate of the α-TEA free acid showing two endotherms with the endotherms at about 56 and 205° C.

The lysine salt of α-TEA is a crystalline solid that is less "waxy" than the free acid. The unique X-ray diffraction pattern of this sample is shown in FIG. 6. The DSC thermogram exhibited multiple endothermic transitions at about 55 and 200° C. The DSC plot is shown in FIG. 7. The total volatile content by TGA over the temperature range 25-168.8° C. was 0.4 wt %.

The $^1$H NMR of the lysine salt shows the stoichiometry of free acid to base to be in a 1:0.7 ratio. A change in chemical shifts from the free acid spectrum was observed suggesting the compound is a salt.

The DVS adsorption isotherm shows onset of weight gain at about 75% RH, with a rapid total weight gain of about 12% at 95% RH. The desorption cycle shows hysteresis, in which upon desorption (decreasing humidity) the sample does not lose the sorbed water. The residual 2 weight % corresponds to a putative hydrate of the lysine salt. The stoichiometry of the hydrated lysine salt is not defined. The kinetic plot indicates the weight change on desorption does not come to equilibrium indicating that hydrate formation may be reversible given enough time. The particle size of this material appears was very small as evidenced by photomicrograph. The salt exhibits some liquid crystal-like behavior, but to a lesser degree than observed with the free acid. The approximate visual solubility of the lysine salt in pH 4, 7, and 10 buffers was <0.2 mg/mL.

d) Choline

Figure 8:
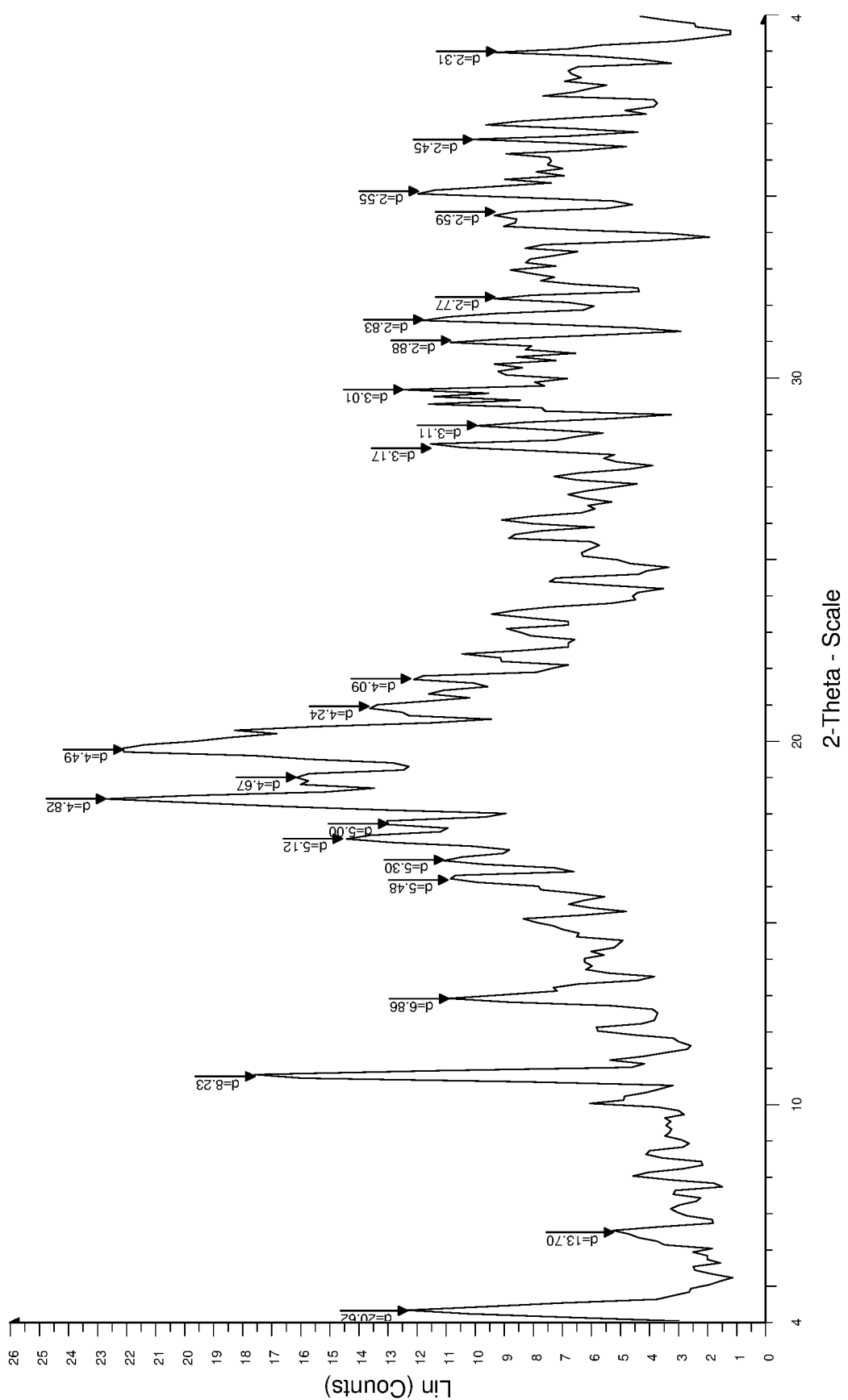
FIG. 8—A CuKα powder x-ray diffractogram of a representative choline salt candidate from panels 1-3. The spectra shows a pair of dominate peaks at about 18.4 and 19.77°2θ.
Figure 9:
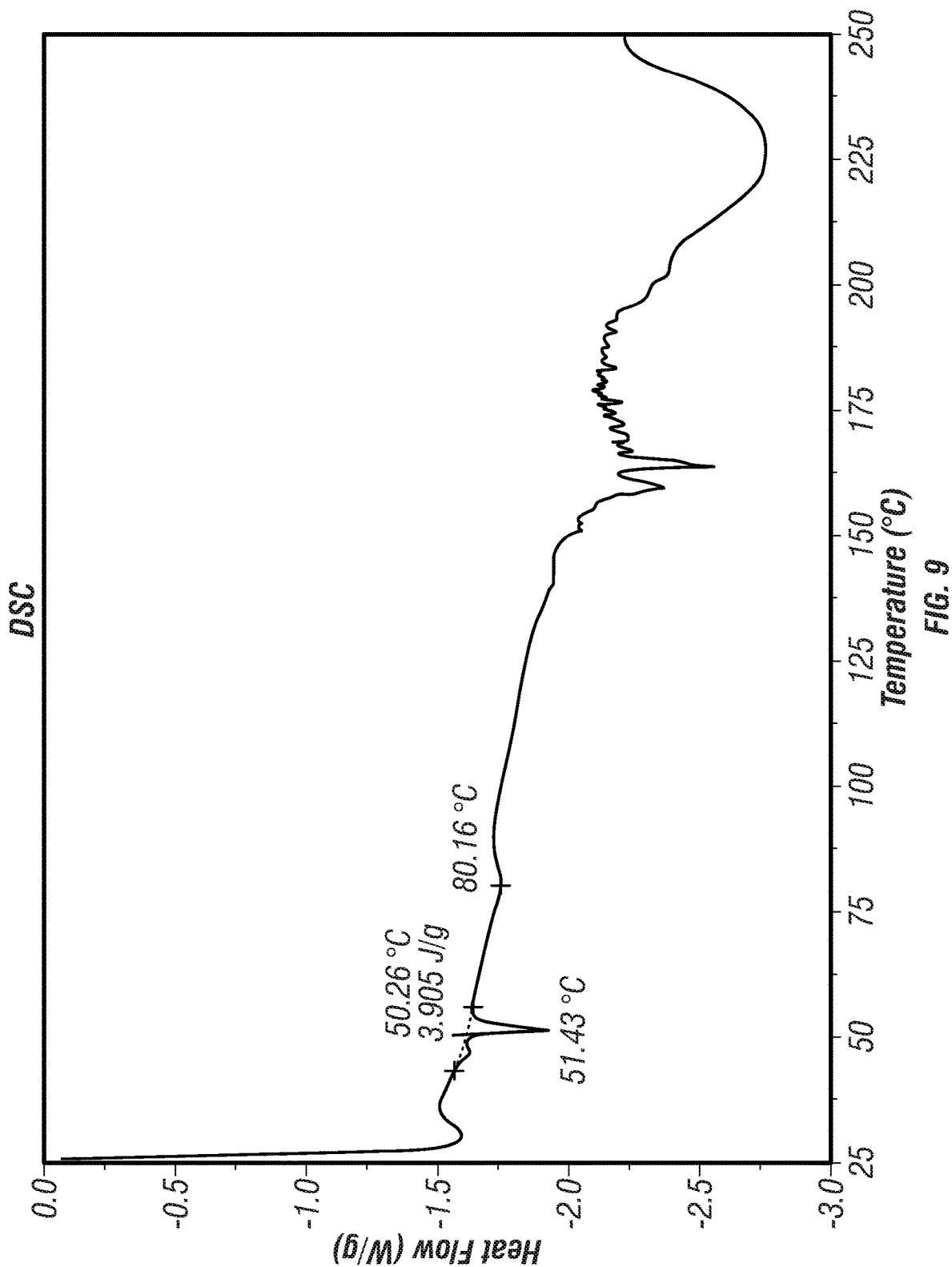
FIG. 9—A differential scanning calorimetry (DSC) isotherm of the choline salt candidate of the α-TEA free acid showing three endotherms with the endotherms at about 50, 80 and 150° C.

The choline salt of α-TEA is a partially crystalline "waxy" solid. The unique X-ray diffraction pattern of the sample was observed is shown in FIG. 8. The DSC thermogram exhibited multiple endothermic transitions at about 50, 80, and 150° C. The DSC plot is shown in FIG. 9. The total volatile content by TGA over the temperature range 25-188.2° C. was 2.5 wt %.

The $^1$H NMR of this candidate shows the stoichiometry of free acid to base to be in a 1:0.8 ratio. A change in chemical shifts from the free acid spectrum was observed suggesting this candidate is a salt.

e) Tris-Hydroxymethyl Amine (Tris)

Figure 10:
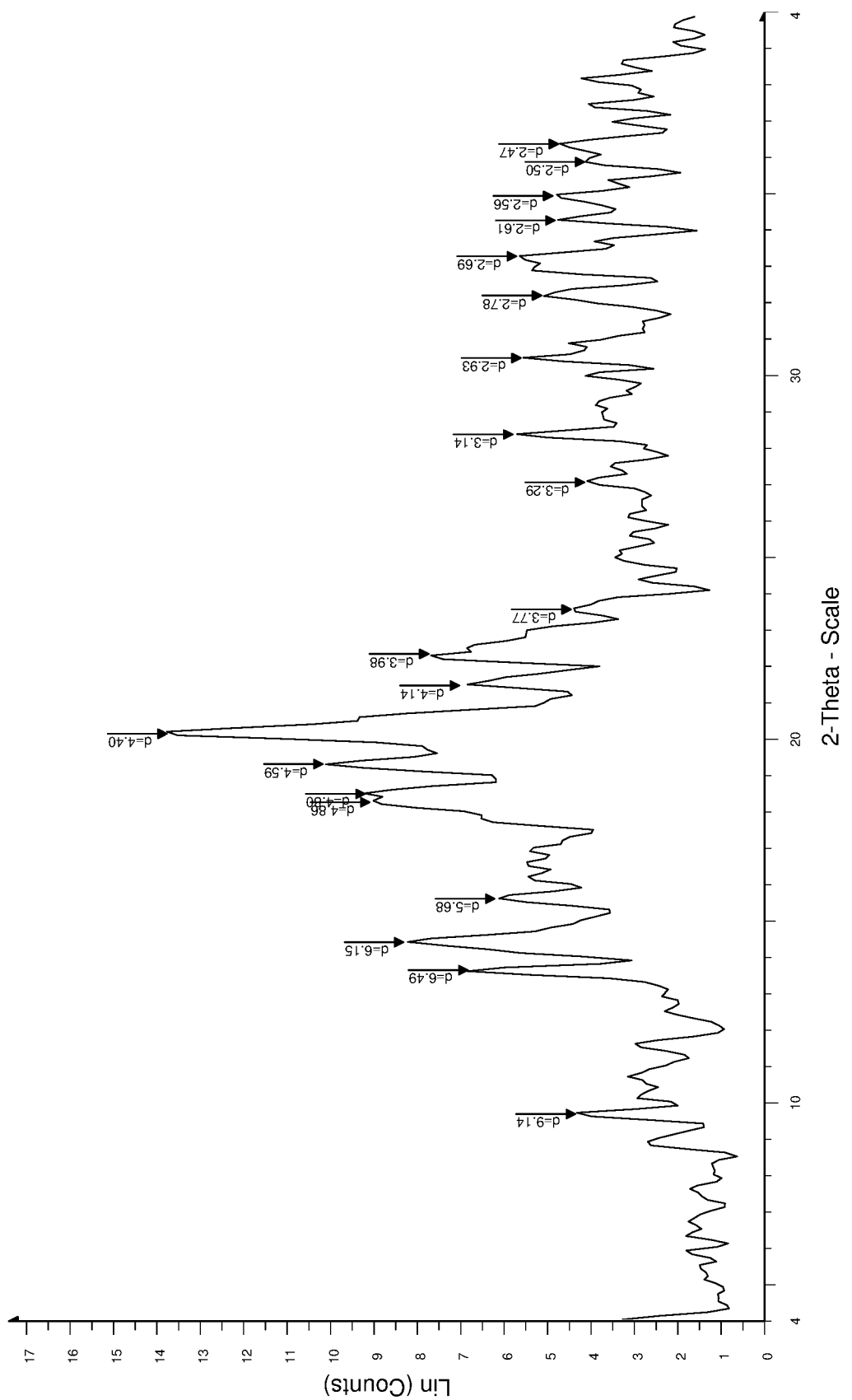
FIG. 10—A CuKα powder x-ray diffractogram of a representative tris salt candidate. The spectra shows a dominate peak at about 20.14°2θ.
Figure 11:
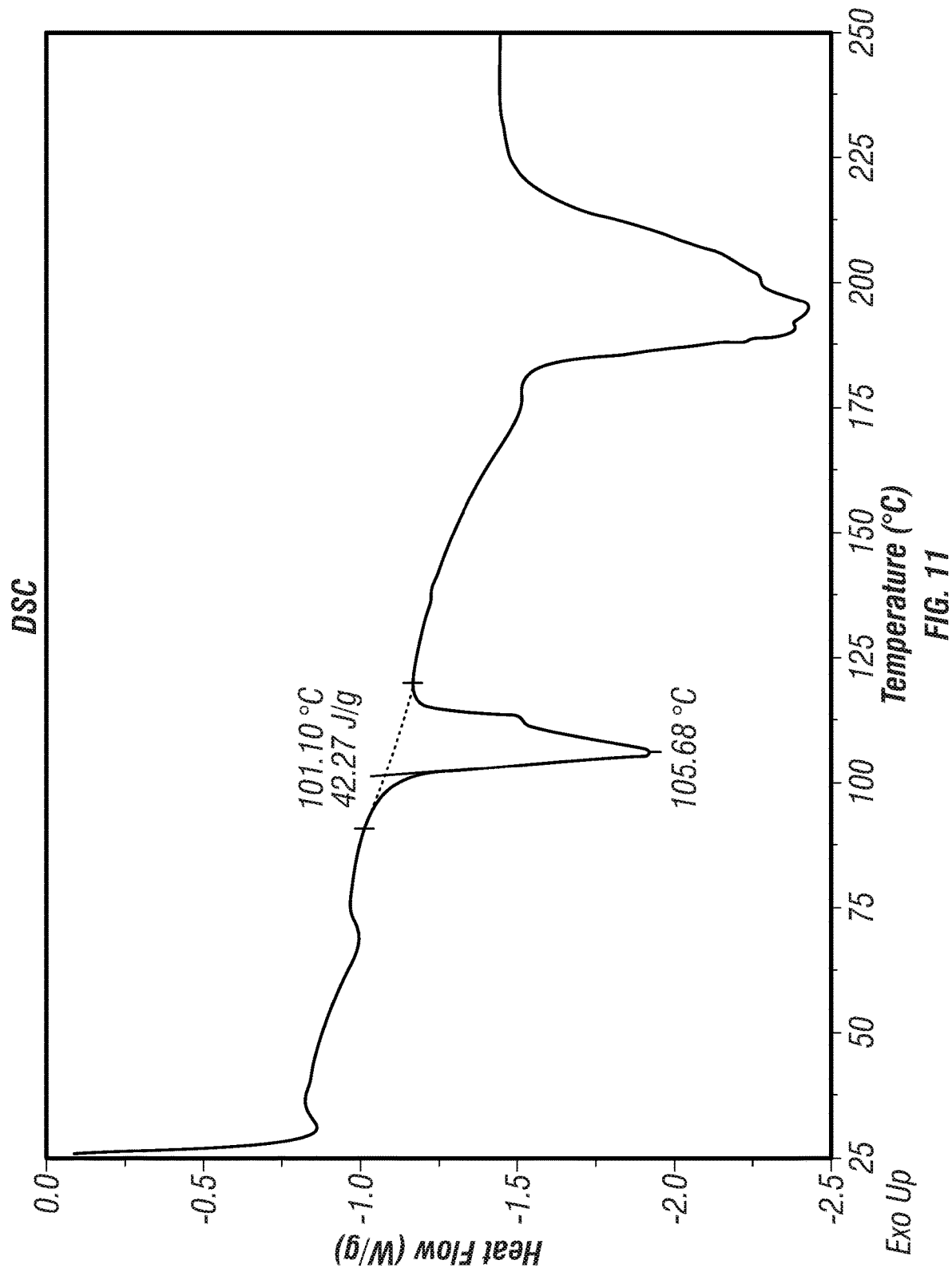
FIG. 11—A differential scanning calorimetry (DSC) isotherm of the tris salt candidate of the α-TEA free acid showing two endotherms with the endotherms at about 106 and 192° C.

The tris candidate was a partially crystalline "semi-waxy" solid. The unique X-ray diffraction pattern of the sample was observed is shown in FIG. 10. The DSC thermogram exhibited multiple endothermic transitions at about 101 and 175° C. The DSC plot is shown in FIG. 11. The total volatile content by TGA over the temperature range 25-144° C. was 0.6 wt %.

The $^1$H NMR of this candidate shows the stoichiometry of free acid to base to be in a 1:1+ ratio. A change in chemical shifts from the free acid spectrum was observed suggesting this candidate is a salt.

The DVS isotherm indicates a possible hemihydrate formation (1.5% weight gain) starting at about 55% RH. The desorption cycle shows hysteresis indicating that the water is well bound. The particle size of this material was very small based upon photomicrograph images. There is some liquid crystal-like behavior, but to a lesser degree than observed with the free acid. The approximate visual solubility of the tris salt in pH 4, 7, and 10 buffers was <0.2 mg/mL.

f) N,N-Dimethylethanolamine (Deanol)

Figure 12:
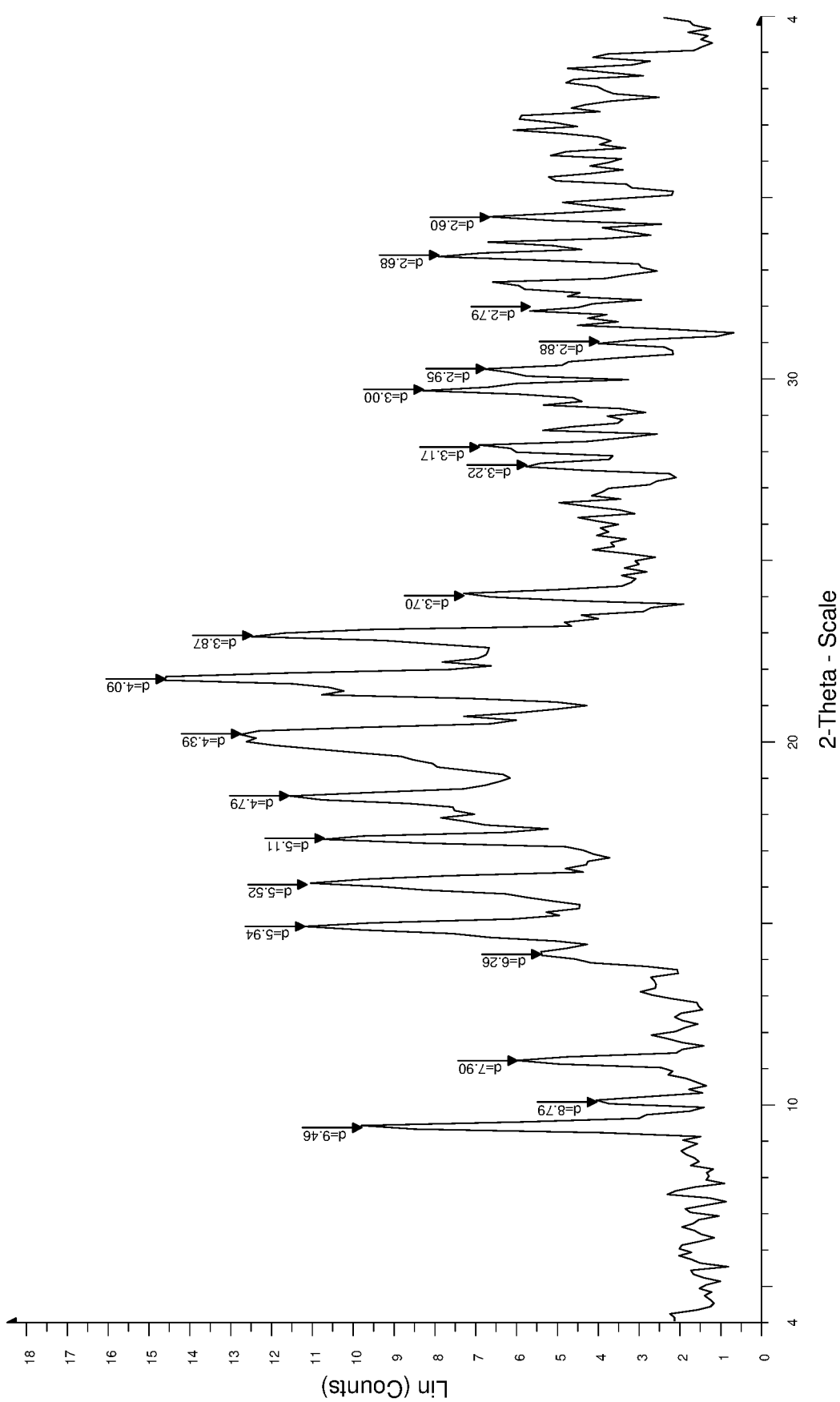
FIG. 12—A CuKα powder x-ray diffractogram of a representative N,N-dimethyl-ethanolamine salt candidate from panels 1-3. The spectra shows a dominate peak at about 21.73°2θ.
Figure 13:
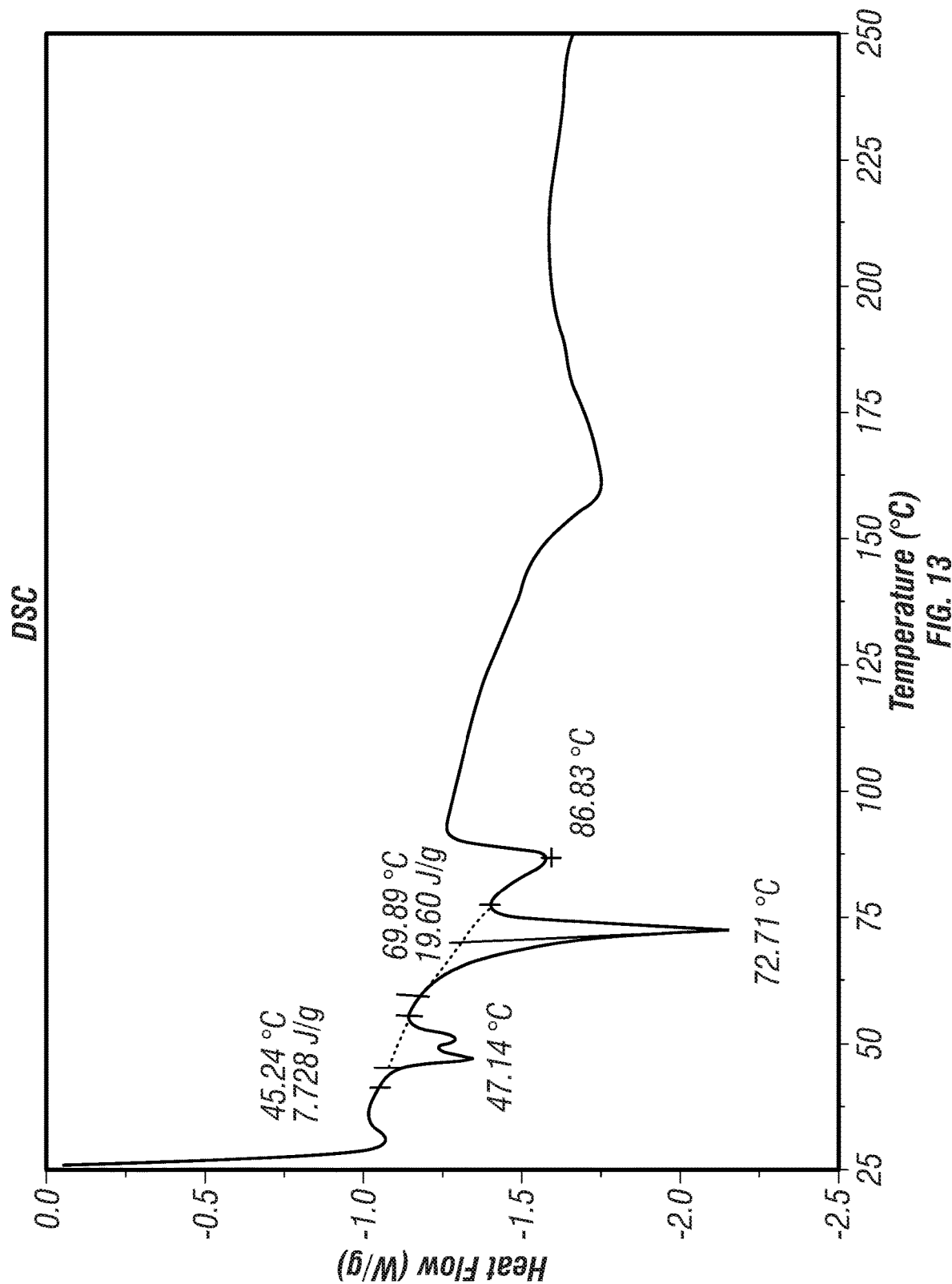
FIG. 13—A differential scanning calorimetry (DSC) isotherm of the N,N-dimethyl-ethanolamine salt candidate of the α-TEA free acid showing three endotherms with the endotherms at about 47, 73, and 87° C.
Figure 14:
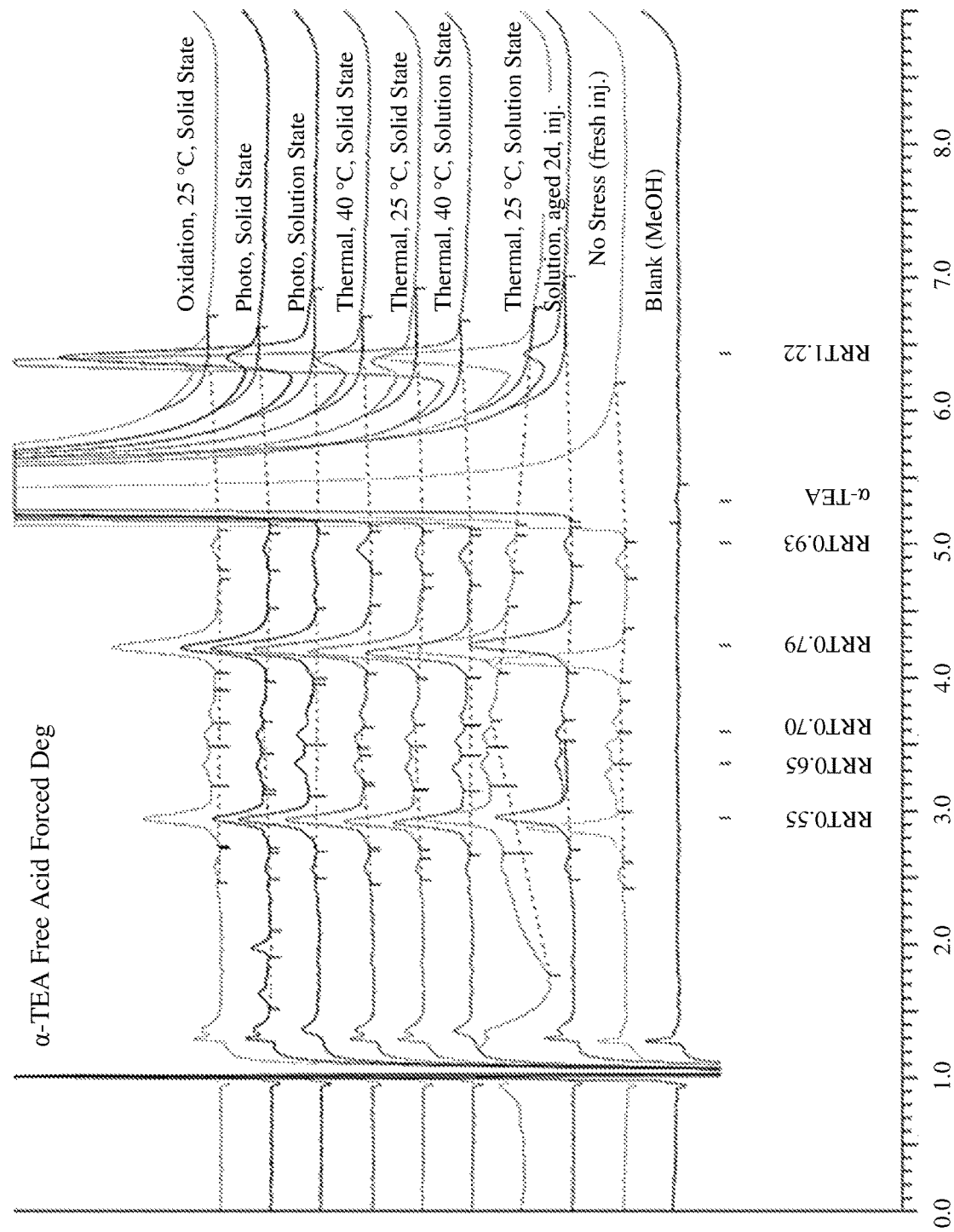
FIG. 14—A graph showing HPLC traces of different α-TEA free acid samples that have been subjected to different stresses to test the stability of the compound in that form.
Figure 15:
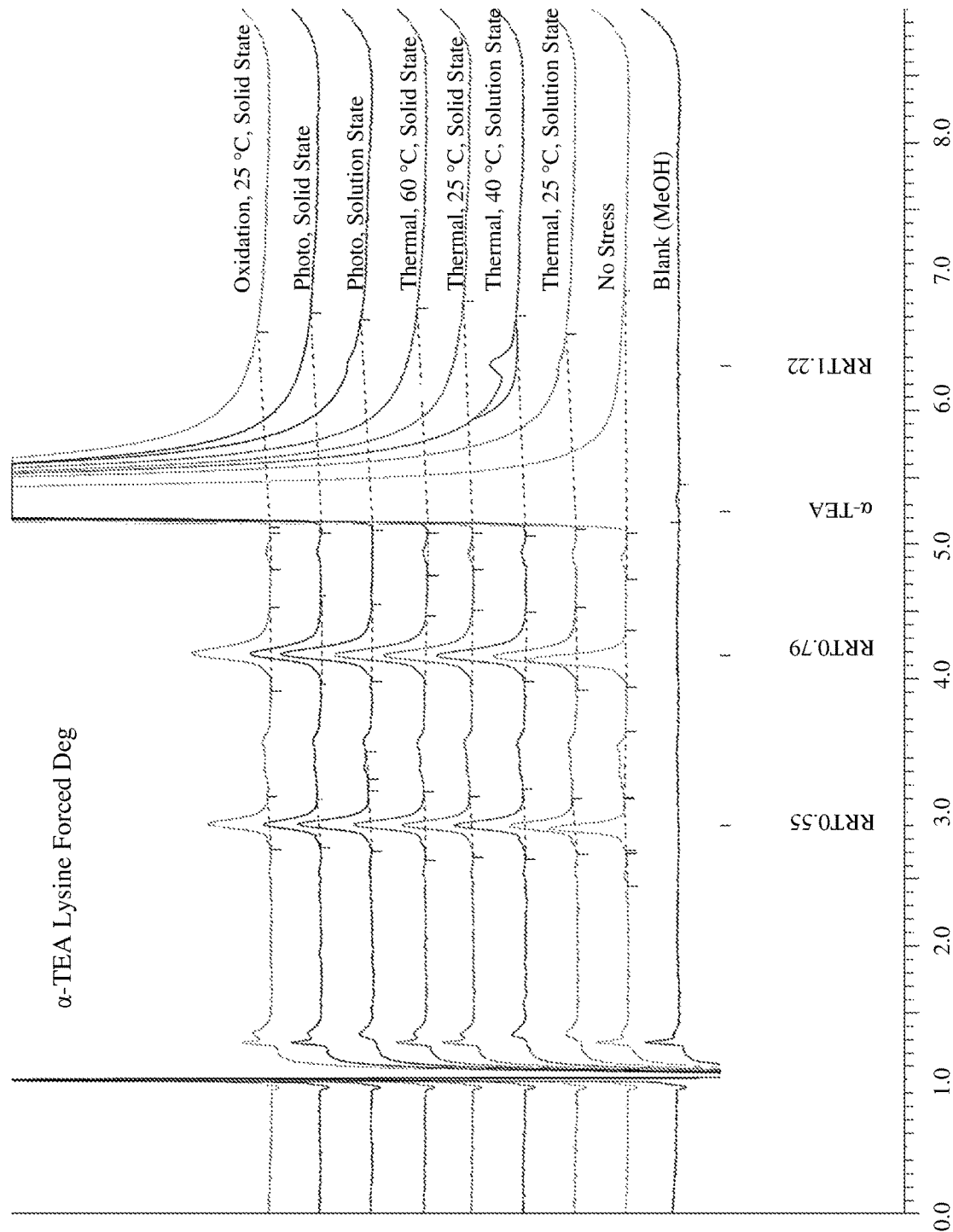
FIG. 15—A graph showing HPLC traces of different α-TEA lysine salt samples that have been subjected to different stresses to test the stability of the compound in that form.
Figure 16:
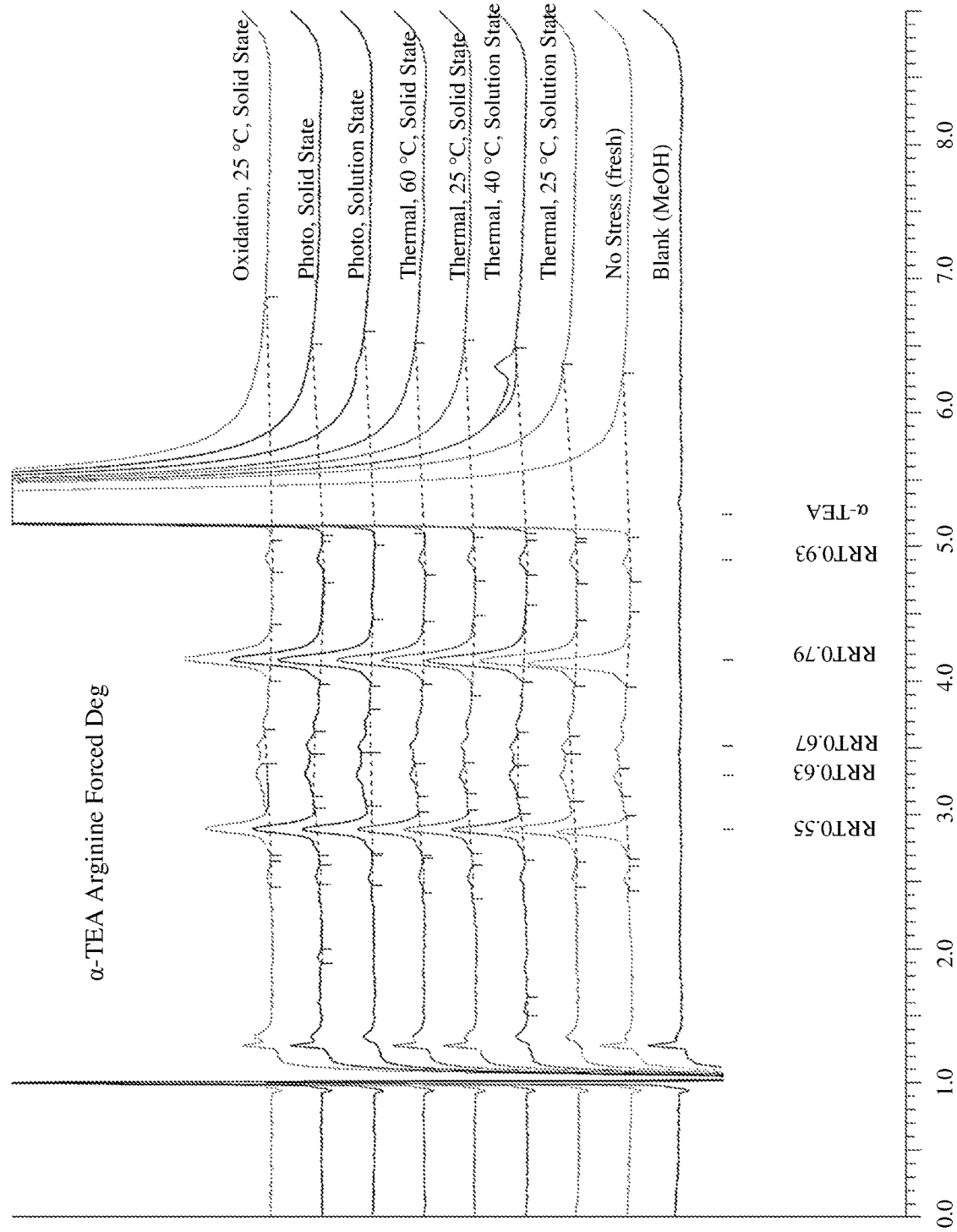
FIG. 16—A graph showing HPLC traces of different α-TEA arginine salt samples that have been subjected to different stresses to test the stability of the compound in that form.
Figure 17:
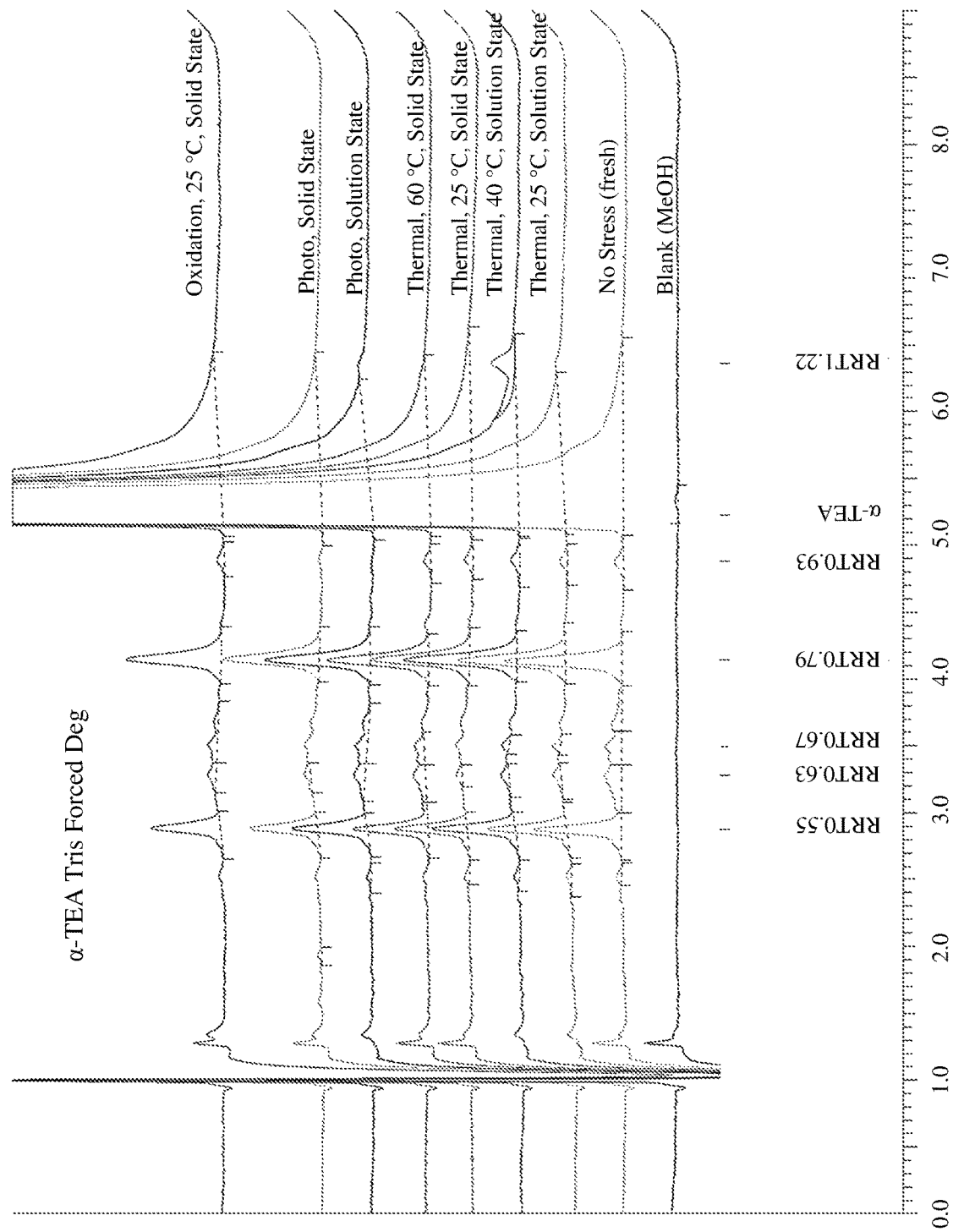
FIG. 17—A graph showing HPLC traces of different α-TEA tris salt samples that have been subjected to different stresses to test the stability of the compound in that form.

The deanol candidate is a crystalline "waxy" solid. The unique X-ray diffraction pattern of the sample was observed is shown in FIG. 12. The DSC thermogram exhibited multiple endothermic transitions at about 47, 73, and 87° C. The DSC plot is shown in FIG. 13. The total volatile content by TGA over the temperature range 25-207° C. was 7.7 wt %.

The $^1$H NMR of this candidate shows the stoichiometry of free acid to base to be in a 1:0.7 ratio. A change in chemical shifts from the free acid spectrum was observed suggesting this candidate is a salt.

4. Salt Screen Scale Up Results and Discussion

Based on results of the primary salt screening panels, the lysine, arginine and Iris monosalts were selected for further investigation. This analysis served two purposes; firstly to provide a sufficient quantity of material for further testing, and secondly, to gather information on the processability and physical handling characteristics of the salt candidates. Samples were analyzed by XRD. DSC, Hot Stage Microscopy (HSM), HPLC for purity, static humidity, stoichiometry, and stability.

a) Lysine (Sample 901)

The scaled-up lysine salt had more desirable handling properties compared to the free acid, including being less "tacky" than the free acid. Furthermore, the salt was a crystalline powder and easier to formulate into a capsule than the free acid.

The XRD pattern of the scaled-up lysine salt candidate was consistent with the pattern of the small scale sample. The DSC profile of this sample is very similar to the small scale sample, both exhibiting endothermic transitions at about 55 and 200° C. Hot stage microscopy (HSM) was carried out on this salt candidate in order to aid in explaining the multiple endotherms observed by DSC. Visual onset of melting was observed at about 200° C. with complete melting by about 215° C. No obvious transition was observed at about 55° C.

The HPLC total area normalization (TAN) purity of the salt was determined to be 98 area % given a relative purity of the compound.

Formation of hydrates can be a very slow kinetic process. A second approach to identify hydrate formation is performing static humidity experiments and monitor gravimetrically for weight change. Samples of lysine salt were placed in 75 and 84% RH environments for 33 and 9 days respectively. After 33 days at 75% RH the lysine sample gained 0.6 weight %. At 84% RH, after 9 days, the lysine salt exhibited a weight gain of 1.8%. The X-ray diffraction pattern of this 84% RH sample showed no change from the prehumidified sample. Given the DVS behavior of the small scale sample, these studies suggest an isostructural hemihydrate exists.

The $^1$H NMR analysis showed this candidate to have a monomolar ratio of free acid to base. The chemical shift of the methylene group in the polar part of the molecule suggests that the compound appears to be a salt.

b) Arginine (Sample 903)

The scaled up arginine salt exhibited better handling relative to the free acid.

The XRD pattern of the scaled up arginine salt matches the pattern of the small scale sample pattern. The DSC profile of this sample matches small scale exhibiting 2 endothermic transitions at about 136, and 187° C. respectively. Hot stage microscopy (HSM) on this salt candidate showed visual melting at about 180° C. and above. No changes in the sample were visually observed in the 130 to 140° C. temperature range. The endothermic transition observed in the DSC profile in this temperature region may be due to a thermally induced liquid crystal phase change. Some variable temperature XRD studies may be useful in studying this transition further.

The HPLC-Total Area Normalization (TAN purity) of the salt was found to be 98 area % given a relative purity of the compound.

Samples of arginine salt were placed in 75 and 84% RH environments for 33 and 9 days respectively. After 33 days at 75% RH the arginine sample gained 0.7 weight %. At 84% RH, after 9 days, the arginine salt exhibited a weight gain of 2.3%. The X-ray diffraction pattern of this 84% RH sample showed no change from the pre-humidified sample, suggesting that if a hydrate is forming, it has the same XRD pattern.

The $^1$H NMR analysis showed this salt to have a mole ratio of free acid to base of one. The chemical shift of the methylene group in the polar part of the molecule suggests that a salt has been formed.

C) Tris (Sample 902)

The scaled up tris salt appears to have more normal handling than the free acid but is slightly waxier than both the lysine and arginine salts.

The XRD pattern of the scaled up tris salt matches small scale sample pattern. The DSC profile is very similar to the small scale sample. The tris scaled up salt exhibits an endotherm with an onset on 106° C. Visual melting was observed using HSM in the 95 to 105° C. temperature range, which corresponds to the endotherm observed in the DSC.

The HPLC-Total Area Normalization (TAN purity) of the salt was found to be 97.5 area % given a relative purity of the compound.

A sample of tris salt was placed in 75% RH environment for 33 days. The sample exhibited a weight gain of 4.0%. This fact is consistent with the DVS data collected earlier.

These data suggest that this salt forms a hydrate upon exposure to sufficient moisture.

The $^1$H NMR analysis showed this salt to have a mole ratio of free acid to base of about one.

The chemical shift of the methylene group in the polar part of the molecule suggests that the compound formed is likely a salt.

A stacked plot of the NMR spectra of the free acid, lysine, arginine, and tris salts shows the movement of the methylene group supporting the conclusion of the formation of salts with the compound.

d) Stability of Salts

The three salts (lysine, arginine, and tris) were challenged using heat (solids stored at 25 and 60° C. for 1 week), oxidation (solids stored in oxygen headspace at 25° C. for 1 week), light (UV source under ICH confirmatory conditions>200 Whr/m$^2$), and solutions (in HPLC diluent) at 25 and 40° C. for 1 week. Stressed samples were analyzed using HPLC to determine their impurity profiles.

A summary of the stability data generated using HPLC analysis is shown below in Table 5.

TABLE 5

Summary of HPLC Stability Data on Stressed Salts

| | HLPC Total Area Normalization - Area % Purity | | | |
|---|---|---|---|---|
| Conditions | Free Add Sample 734 | Lysine Sample 901 | Arginine Sample 903 | Tris Sample 902 |
| Solid State Ambient | 97.8 | 98.8 | 98.6 | 98.6 |
| Solid State 60° C. | 98.0 | 98.7 | 98.6 | 98.4 |
| Solution Ambient Methanol | 96.0 | 98.8 | 98.4 | 98.5 |
| Solution 40° C. Methanol | 94.6 | 98.2 | 98.2 | 98.2 |
| Oxidation Ambient | 97.8 | 98.8 | 98.4 | 98.5 |
| Photo Stability Dark Control | 97.7 | 98.7 | 97.9 | 98.2 |

TABLE 5-continued

Summary of HPLC Stability Data on Stressed Salts

| | HLPC Total Area Normalization - Area % Purity | | | |
|---|---|---|---|---|
| Conditions | Free Add Sample 734 | Lysine Sample 901 | Arginine Sample 903 | Tris Sample 902 |
| Photo Stability Exposed | 98.2 | 98.8 | 98.5 | 98.7 |

The stability results shown in Table 5 represent the averages of two injections of duplicate sample preparations. While the data can only suggest the short term stability, they do provide some insight into the stability of the salt forms which could be extrapolated to the salts long term stability. FIGS. 14-17 show the chromatogram overlay plots for samples analyzed during the stability portion of the study. The HPLC stability data show that the salts exhibited little to no degradation under the stress conditions used in the study. All three salt candidates show improved solution stability in methanol compared to the free acid.

5. Summary of Salt Screening Studies

A salt screening study was performed to identify suitable salt candidates of α-TEA. During the course of the study, 16 different potential bases were examined. Of these bases, 6 bases formed crystalline salts. The most promising of the group, salts of lysine, arginine, and tris were isolated and studied in detail. These three salts were scaled-up to 2 grams and evaluated using multiple analytical techniques.

Based on the data obtained during this study, all three of these salts appear to be viable candidates. These salts exhibit improved physical properties over the free acid. All of the salts are crystalline and have less "waxy" physical properties relative to the free acid. The lysine and arginine salts exhibit the most improvement in this characteristic. The visual melting temperature of all three salts is higher than the free acid. All three salts exhibit equal stability under all conditions tested with improved stability over the free acid in solution. The visual solubility of each salt was comparable to the free acid in buffered water (<0.2 mg/mL).

The salt samples all exhibited the potential to form putative hydrates all which appear to be reversible. The arginine and tris salts exhibited DVS water uptake near critical humidities, 40% and 55% RH respectively. The lysine salt shows DVS water uptake above about 75% RH.

TABLE 6

Summary of Final Salt Characteristics

| Salt | Physical handling as compared to free acid | XRD | Visual melting compared to free acid | Stability compared to free acid | Hydration properties | | Counter Ion Class |
|---|---|---|---|---|---|---|---|
| | | | | | DVS | Static 75% RH 30 Days | |
| lysine | better | crystalline | higher, ~200° C. | more stable in solution | ~75% RH hydrate | 0.6 wt% gain | I |
| arginine | better | crystalline | higher, ~180° C. | more stable in solution | ~40% RH hemihydrate | 0.7 wt % gain | I |
| tris | better | crystalline | higher, ~100° C. | more stable in solution | ~55% RH hemihydrate | 4.0 wt % gain | II |

C. Anti-Tumor Efficacy of α-TEA Salts in Animal Models

Figure 18:
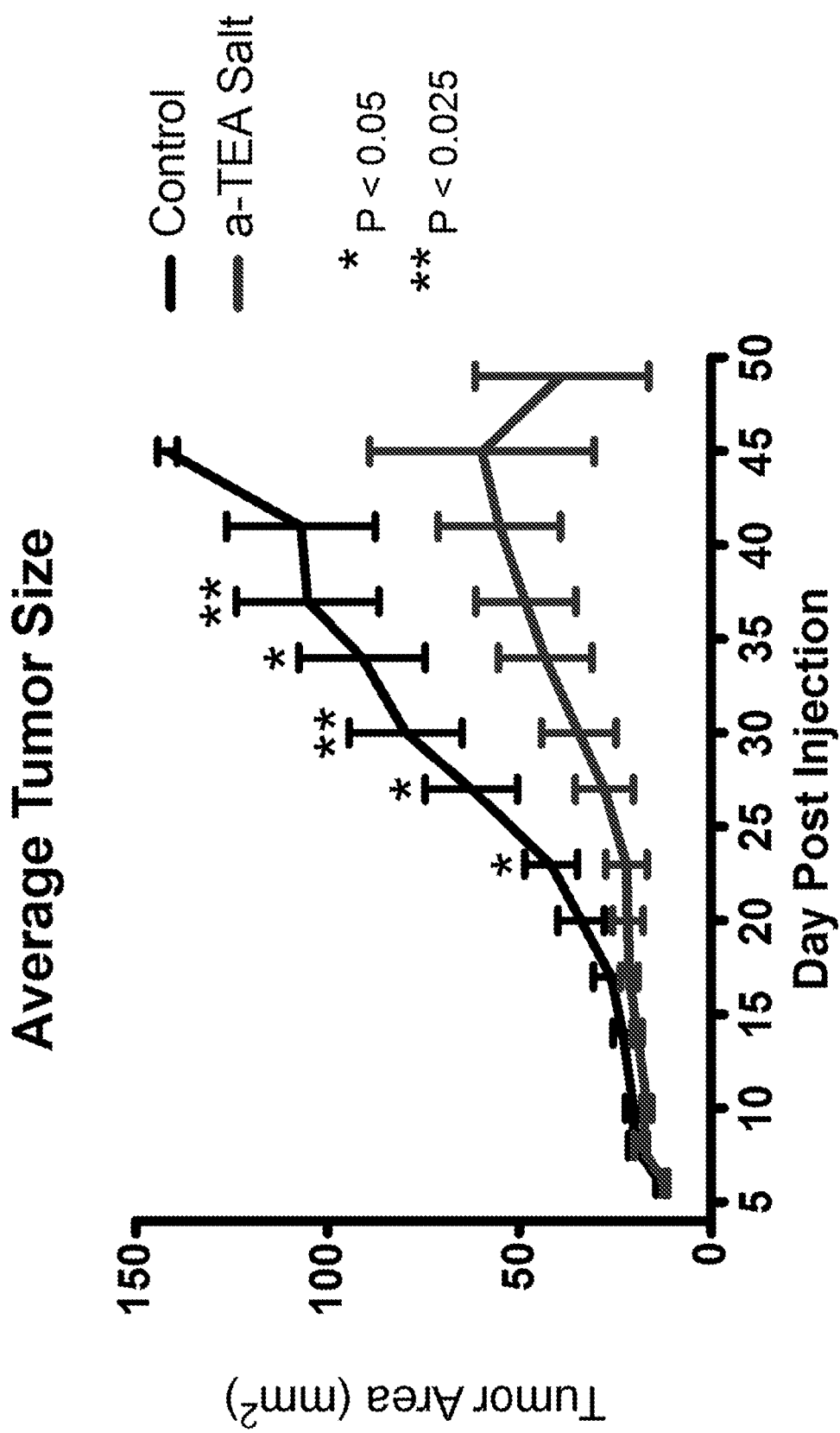
FIG. 18—A graph of the average tumor size of BALB/c mice with a 4T1 mammary tumor in mammary fat pad for control group and mice feed a diet which contained the α-TEA lysine salt.
Figure 19:
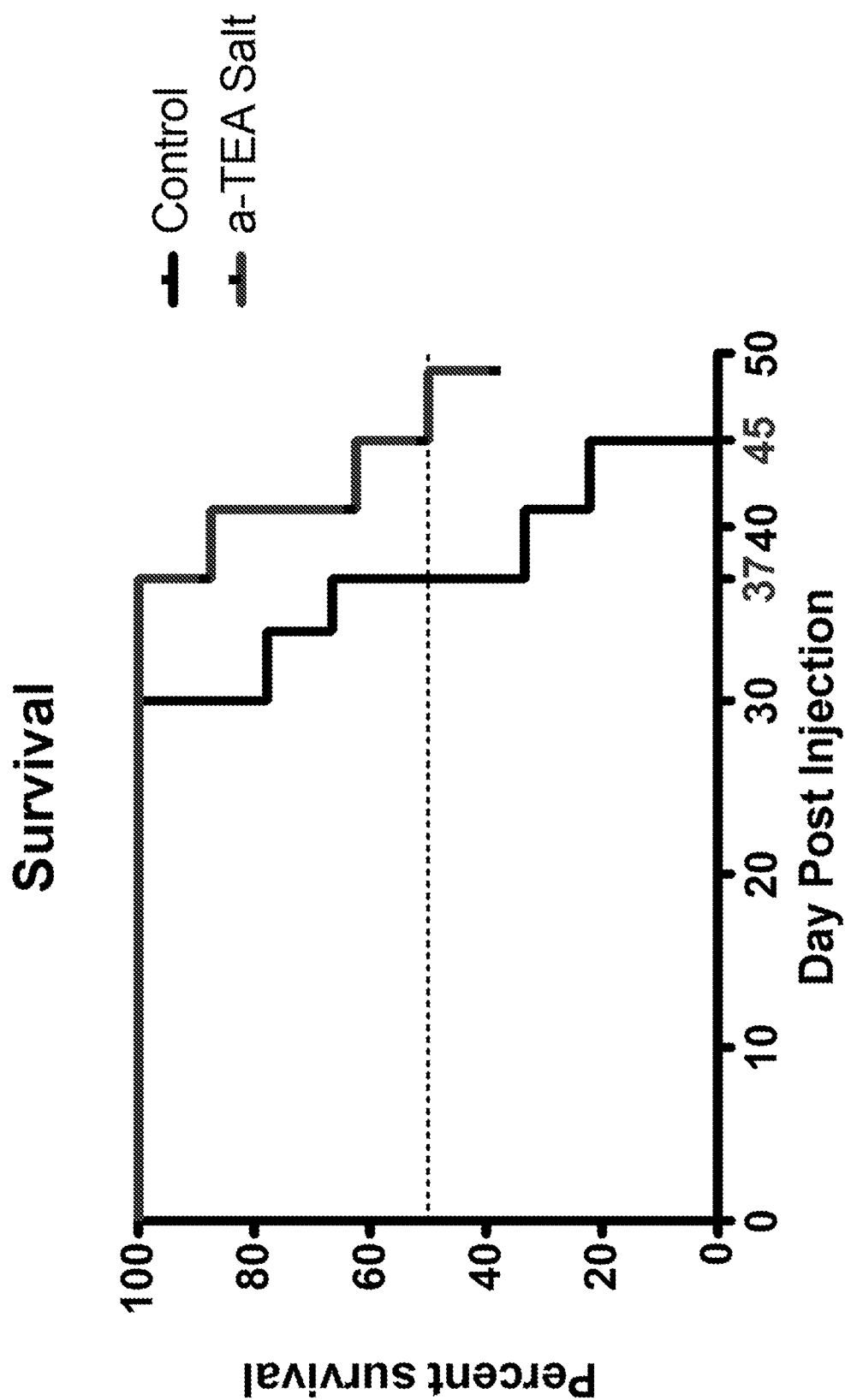
FIG. 19—A graph of the Kaplan-Meier analysis of survival of the BALB/c mice on a diet of α-TEA lysine salt compared to mice fed a nutrient analogous control diet.

Studies of the anti-tumor efficacy of the α-TEA salts were carried out using a well characterized but difficult to treat 4TI mouse model of metastatic mammary cancer with the α-TEA lysine salt (α-TEA-Lys). The lysine salt was incorporated into standard mouse chow at an amount of 3 g/kg chow (0.3% w/w) by Harlan Teklad, Madison Wis. Half of the mice were placed on an α-TEA-Lys diet after the tumors were established (9 days post tumor injection.) and the rest placed on an analogous nutrient diet without α-TEA-Lys which served as the control group. The average tumor size of mice that ate a diet containing α-TEA-Lys showed a significant decrease in average tumor size compared to mice feed a control diet without the α-TEA salt (FIG. 18). Furthermore, mice consuming a diet which contains the α-TEA salt showed an increased survival compared to mice who consumed a control diet of standard chow (FIG. 19). These data suggest that converting α-TEA into a salt appear to have little change on the efficacy of the compound with significant tumor growth suppression, prolongation of overall survival, and complete tumor regression in about 25% of the mice treated.

All of the compounds, polymorphs, formulations, and methods disclosed and claimed herein can be made and executed without undue experimentation in light of the present disclosure. While the compounds, polymorphs, formulations, and methods of this invention have been described in terms of preferred embodiments, it will be apparent to those of skill in the art that variations may be applied to the compounds, polymorphs, formulations, and methods, as well as in the steps or in the sequence of steps of the method described herein without departing from the concept, spirit, and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references to the extent that they provide exemplary procedural or other details supplementary to those set forth herein, are specifically incorporated herein by reference.

U.S. Pat. No. 6,417,223
U.S. Pat. No. 6,703,384
U.S. Pat. No. 6,770,672
U.S. Pat. No. 7,312,232
Anderson, et al., *Cancer Res*, 64:4263-4269, 2004.
Hahn, et al., *Cancer Res*, 66:9374-9378, 2006.
Hahn, et al., *Mol Cancer Ther*, 8:1570-1578, 2009.
Hahn, et al., *BMC Cancer*, 11:471, 2011.
Kline, et al., *Vitam Horm*, 76:435-461, 2007.
Lawson, et al., *Cancer Chemother Pharmacol*, 54:421-431, 2004.
*March's Advanced Organic Chemistry: Reactions, Mechanisms, and Structure*, 2007.
Neuzil, et al., *Mol Aspects Med*, 28:607-645, 2007.
Yu, et al., *Mol Carcinog*, 49:964-973, 2010.

What is claimed is:

1. A method of treating a cancer, comprising administering to a patient a therapeutically effective amount of a compound of the formula:

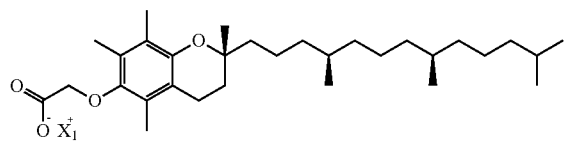

wherein $X_1^+$ is:

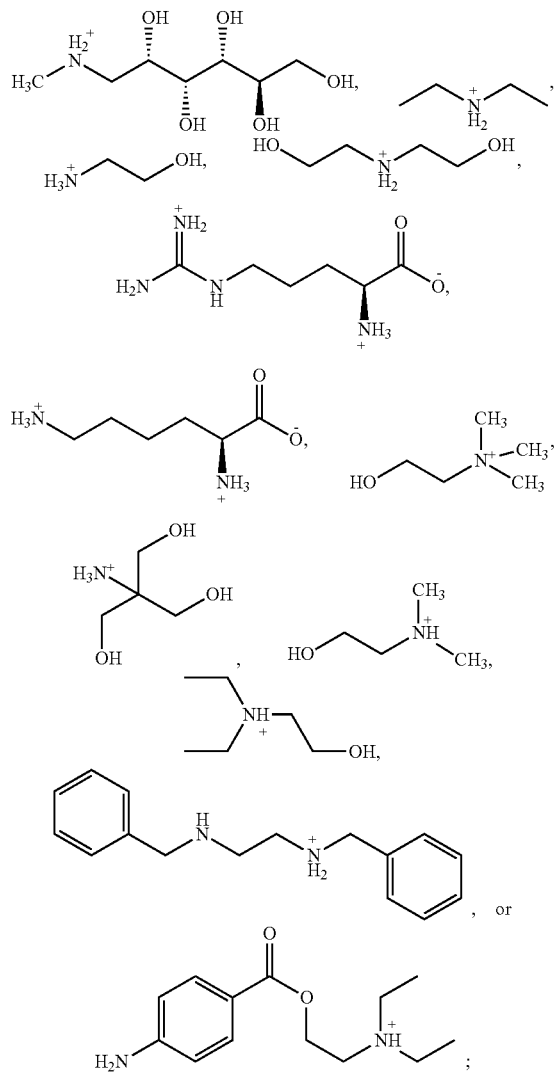

or a hydrate thereof;
wherein the cancer is a breast cancer.

2. The method of claim 1, further comprising administering to the patient a second therapy.

3. The method of claim 2, wherein the second therapy is an immunotherapy, radiotherapy, chemotherapeutic agent, or surgery.

4. The method of claim 3, wherein the second therapy is an immunotherapy.

5. The method of claim 4, wherein the immunotherapy comprises administering a pharmaceutically effective amount of adoptively transferred T lymphocytes, an immune modulating antibody, or a therapeutic antibody.

6. The method of claim 5, wherein the immunotherapy comprises administering a pharmaceutically effective amount of trastuzumab.

7. The method of claim 5, wherein the immunotherapy comprises administering adoptively transferred T lymphocytes to the patient.

8. The method of claim 7, wherein the adoptively transferred T lymphocytes are engineered to express a chimeric antigen receptor (CAR).

9. The method of claim 5, wherein the therapeutic antibody is an anti-PD-1, anti-4-1-BB, anti-GITR, anti-TIM3, anti-LAG3, anti-TIGIT, anti-CTLA-4 or an anti-LIGHT antibody.

10. The method of claim 3, wherein the chemotherapeutic agent is an anthracycline, a taxane, methotrexate, mitoxantrone, estramustine, doxorubicin, etoposide, vinblastine, carboplatin, vinorelbine, 5-fluorouracil, cisplatin, topotecan, ifosfamide, cyclophosphamide, epirubicin, gemcitabine, vinorelbine, irinotecan, etoposide, vinblastine, pemetrexed, melphalan, capecitabine, oxaliplatin, a BRAF inhibitor, or a TGF-beta inhibitor.

11. The compound of either claim 1, wherein the $X_1^+$ is:

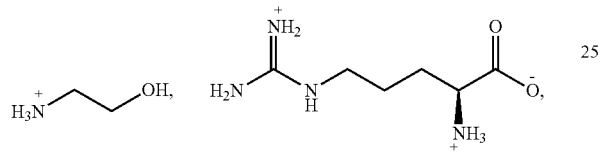

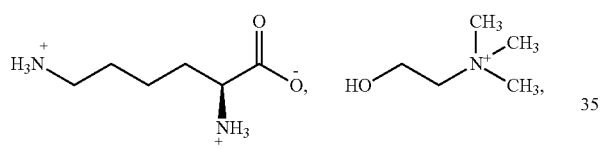

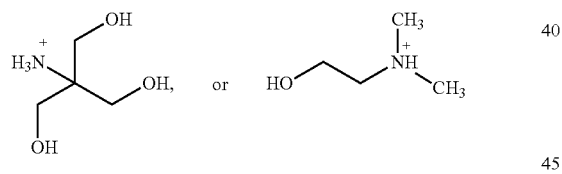

or a hydrate, thereof.

12. The compound of claim 11, wherein the $X_1^+$ is

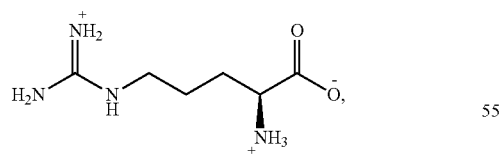

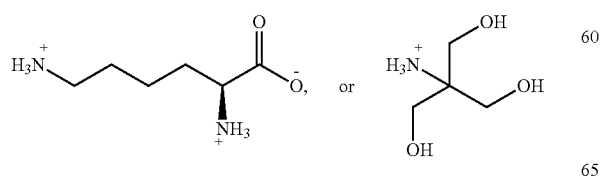

or a hydrate, thereof.

13. The compound of claim 1, wherein the formula is further defined as:
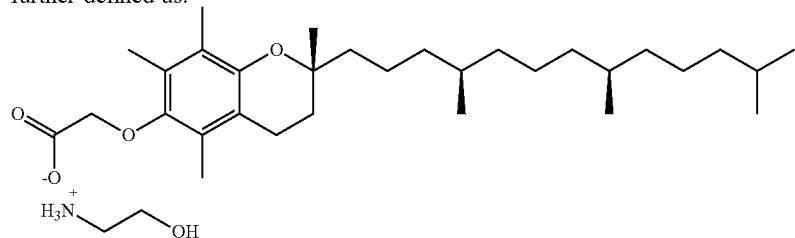
or a hydrate, thereof.
14. The compound of claim 1, wherein the formula is further defined as:
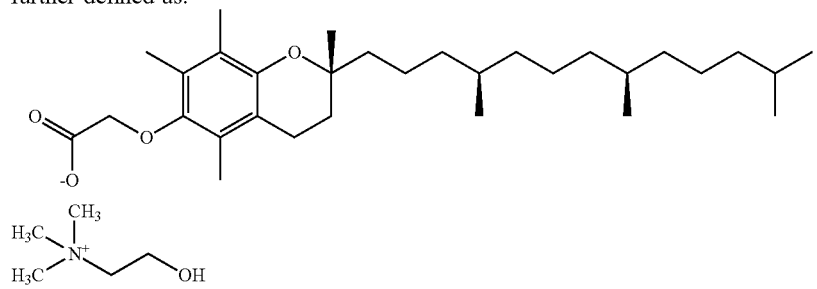
or a hydrate, thereof.
15. The compound of claim 1, wherein the formula is further defined as:
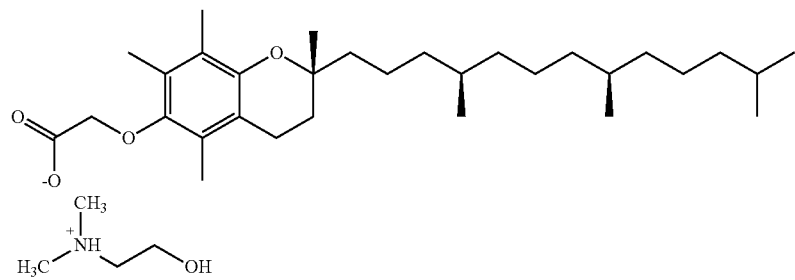
or a hydrate, thereof.
16. The compound of claim 1, wherein the formula is further defined as:
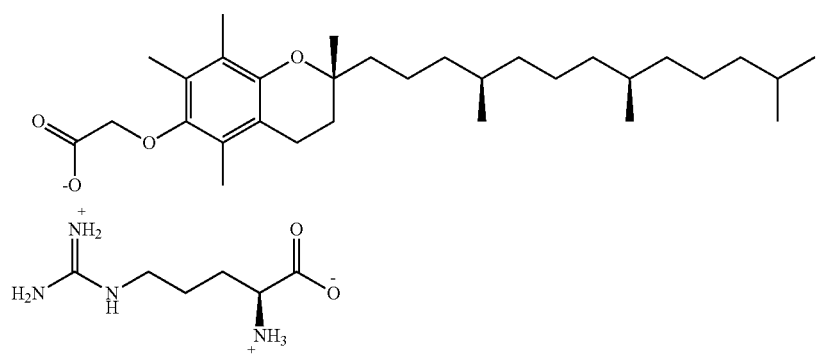
or a hydrate, thereof.
* * * * *